US010012656B2

(12) United States Patent
Espiner et al.

(10) Patent No.: US 10,012,656 B2
(45) Date of Patent: Jul. 3, 2018

(54) NT-PROCNP AS A BIOMARKER OF VASCULAR DISORDERS AND PREGNANCY COMPLICATION

(71) Applicant: Otago Innovation Limited, Dunedin (NZ)

(72) Inventors: Eric Arnold Espiner, Christchurch (NZ); Timothy Charles Ramsey Prickett, Christchurch (NZ)

(73) Assignee: Otago Innovation Limited, Dunedin (NZ)

( * ) Notice: Subject to any disclaimer, the term of this patent is extended or adjusted under 35 U.S.C. 154(b) by 530 days.

(21) Appl. No.: 14/421,423

(22) PCT Filed: Aug. 13, 2013

(86) PCT No.: PCT/NZ2013/000142
§ 371 (c)(1),
(2) Date: Feb. 12, 2015

(87) PCT Pub. No.: WO2014/027899
PCT Pub. Date: Feb. 20, 2014

(65) Prior Publication Data
US 2015/0241451 A1    Aug. 27, 2015

Related U.S. Application Data

(60) Provisional application No. 61/682,729, filed on Aug. 13, 2012.

(51) Int. Cl.
  *G01N 33/68*    (2006.01)
  *C07K 16/22*    (2006.01)
  *G01N 33/74*    (2006.01)

(52) U.S. Cl.
  CPC ......... *G01N 33/6893* (2013.01); *C07K 16/22* (2013.01); *G01N 33/74* (2013.01); *G01N 2333/4703* (2013.01); *G01N 2333/58* (2013.01); *G01N 2800/226* (2013.01); *G01N 2800/32* (2013.01); *G01N 2800/52* (2013.01)

(58) Field of Classification Search
  None
  See application file for complete search history.

(56) References Cited

U.S. PATENT DOCUMENTS 7,618,943 B2    11/2009  Berdel et al.
7,919,255 B2 *   4/2011  Prickett .................. C07K 16/26
                                                        435/7.1

FOREIGN PATENT DOCUMENTS

WO        01/14885 A2      3/2004
WO     2004/099139 A1     11/2004
WO     2008/042855 A2      4/2008
WO     2011/157445 A1     12/2011
WO     2013/095759 A1      6/2013

OTHER PUBLICATIONS

Zakeri et al. (Circulation, 2011, vol. 124, No. 21, Suppl.S, A10128, Abstract).*
Prickett et al. (Biochem. Biophys. Res. Comm. 286: 513, 2001).*
Naruko et al., "C-Type Natriuretic Peptide in Human Coronary Atherosclerotic Lesions," *Circulation* 1996; 94: 3103-3108.
Casco et al., "Natriuretic Peptide System Gene Expression in Human Coronary Arteries," *The Journal of Histochemistry & Cytochemistry* 50(6):799-809, 2002.
Cole, "The LMS method for constructing normalized growth standards," *European Journal of Clinical Nutrition* 44:45-60, 1990.
Del Ry et al., "Comparison of NT-proCNP and CNP plasma levels in heart failure, diabetes and cirrhosis patients," *Regulatory Peptides* 166:15-20, 2011.
Dutta et al., "Myocardial infarction accelerates atherosclerosis," *Nature* 487(7407):325-329, 2012.
Espiner et al., "Effects of pre-eclampsia and fetal growth restriction on C-type natriuretic peptide," *BJOG* 122:1236-1243, 2015.
Extended European Search Report, dated May 31, 2016, for European Application No. 13829360.0-1408 / 2883060, 17 pages.
Hennessy, "Precursors to pre-eclampsia: are there markers in the fetal circulation?," *Clinical Science* 106:449-450, 2004.
Huse et al., "Generation of a Large Combinatorial Library of the Immunoglobulin Repertoire in Phage Lambda," *Science* 246(4935):1275-1281, 1989.
International Preliminary Report on Patentability, dated Feb. 17, 2015, for International Application No. PCT/NZ2013/000142, 8 pages.
Jones et al., "Elastic Lamina Defects are an Early Feature of Aortic Lesions in the Apolipoprotein E Knockout Mouse," *Journal of Vascular Research* 42:237-246, 2005.
Koch, "Serum NT-proCNP concentrations are elevated in patients with chronic liver diseases and associated with complications and unfavorable prognosis of cirrhosis," *Clinical Biochemistry* 45:429-435, 2012.
Köhler et al., "Continuous cultures of fused cells secreting antibody of predefined specificity," *Nature* 256(5517):495-497, 1975.
Levey et al., "A More Accurate Method to Estimate Glomerular Filtration Rate from Serum Creatinine: A New Prediction Equation," *Annals of Internal Medicine* 130(6):461-470, 1999.
McDowell et al., "Anthropometric Reference Data for Children and Adults: United States, 2003-2006," *National Health Statistics Reports* 10:1-45, 2008.
McNeill et al., "C-Type Natriuretic Peptide Forms in Pregnancy: Maternal Plasma Profiles during Ovine Gestation Correlate with Placental and Fetal Maturation," *Endocrinology* 150(10):4777-4783, 2009.
Myatt et al., "Vascular biology of preeclampsia," *Journal of Thrombosis and Haemostasis* 7:375-384, 2009.

(Continued)

*Primary Examiner* — Lisa V Cook
(74) *Attorney, Agent, or Firm* — Medler Ferro Woodhouse Mills pllc

(57) ABSTRACT

The present disclosure relates to methods for the prognosis and/or diagnosis of vascular-related disorders in a subject and in particular pregnancy-related vascular disorders. The present disclosure is based on the finding that a positive correlation exists between positive prediction of a vascular disorder event in a subject and the concentration of the circulating marker NTproCNP (also referred to as NT-CNP) in humans and animals. In addition, the present disclosure is based on the finding that there is also a positive correlation between the occurrence of a vascular related adverse event during pregnancy and the concentration of the circulating marker NT-proCNP in the maternal circulation.

5 Claims, 9 Drawing Sheets

(56) References Cited

OTHER PUBLICATIONS

Naruko et al., "C-type natriutretic peptide in human coronary atherosclerotic lesions," File Medline (STN) Accession No. 97143105, PubMed IDS: 8989116, 1996, 2 pages.
Olney et al., "Amino-terminal propeptide of C-type natriuretic peptide (NTproCNP) predicts height velocity in healthy children" *Clin Endocrinol* 77(3):416-422, 2012.
Prickett et al., "Amino-Terminal proCNP: A Putative Marker of Cartilage Activity in Postnatal Growth," *Pediatric Research* 58(2):334-340, 2005.
Prickett et al., "Identification of Amino-Terminal Pro-C-Type Natriuretic Peptide in Human Plasma," *Biochemical and Biophysical Research Communications* 286:513-517, 2001.
Prickett et al., "N-terminal pro-C-type natriuretic peptide, but not C-type natriuretic peptide, is greatly elevated in the fetal circulation," *Clinical Science* 106:535-540, 2004.
Reid et al., "C-Type Natriuretic Peptide in Complicated Pregnancy: Increased Secretion Precedes Adverse Events," *J Clin Endocrinol Metab* 99(4):1470-1478, 2014.
Schouten et al., "C-Type natriuretic peptide forms in adult hyperthyroidism: correlation with thyroid hormones and markers of bone turnover," *Clinical Endocrinology* 76:790-796, 2012.
Schouten et al., "Central and peripheral forms of C-type natriuretic peptide (CNP): Evidence for differential regulation in plasma and cerebrospinal fluid," *Peptides* 32:797-804, 2011.
Stepan et al., "Detection of C-type natriuretic peptide in normal pregnancy," *J Perinat. Med.* 26:56-58, 1998.
Sugulle et al., "Cardiovascular Biomarker Midregional Protrial Natriuretic Peptide During and After Preeclamptic Pregnancies," *Hypertension* 59(part 2):395-401, 2012.
Vlachopoulos et al., "Amino-terminal pro-C-type natriuretic peptide is associated with arterial stiffness, endothelial function and early atherosclerosis," *Atherosclerosis* 211:649-655, 2010.
Walther et al., "C-type natriuretic peptide in reproduction, pregnancy and fetal development," *Journal of Endocrinology* 180:17-22, 2004.
Wright et al, "Amino-Terminal Pro-C-Type Natriuretic Peptide in Heart Failure," *Hypertension* 43:94-100, 2004.
Wyatt et al., "The Correlation Between Sampling Site and Gene Expression in the Term Human Placenta," *Placenta* 26: 372-379, 2005.
Yandle et al., "The Ovine Hypothalamus and Pituitary Have Markedly Different Distributions of C-Type Natriuretic Peptide Forms," *Peptides* 14:713-716, 1993.
Zakeri et al., "NT-pro C-type Natriuretic Peptide is a Novel Urinary Biomarker with Prognostic Value in Hospitalized Heart Failure Patients Independent of Glomerular Filtration Rate," *Circulation* 124(21), Abstract Only, Abstract No. 10128, 2011. (2 pages).

* cited by examiner

NT-PROCNP AS A BIOMARKER OF VASCULAR DISORDERS AND PREGNANCY COMPLICATION

RELATED APPLICATIONS AND INCORPORATION BY REFERENCE

All documents cited or referenced herein, and all documents cited or referenced in herein cited documents, together with any manufacturer's instructions, descriptions, product specifications, and product sheets for any products mentioned herein or in any document incorporated by reference herein, are hereby incorporated herein by reference in their entirety.

FIELD OF THE INVENTION

The present disclosure relates to methods for the prognosis and/or diagnosis of vascular-related disorders in a subject and in particular pregnancy-related vascular disorders.

BACKGROUND OF THE INVENTION

Vascular disorders, including vascular disorders associated with or contributing to complications in pregnancy often go undetected in subjects. Consequently, there is a need for improved methods for early prediction of vascular disorders in subjects at risk, and preferably before the disorder develops. While several risk factors predicting coronary heart disease or stroke have been identified, including hypertension, hyperlipidaemia, family history, diabetes and smoking, vascular events occur in up to 30% of subjects without these adverse risk factors. Despite optimal management of conditions manifested by such vascular disorders, vascular events continue to occur (in 10-20% of subjects per year) after presentation. Such facts underline the need for a better understanding of vascular disorders and improved means of detection and monitoring.

For example, a biomarker predictive of risk of a vascular disorder in a subject would improve treatment prospects by identifying those subjects before the development of pathological changes threatening organ function and/or adverse event occurrence during pregnancy, and hence would allow specific therapies to be individualised to at risk subjects.

C-type natriuretic peptide (CNP) belongs to a family of natriuretic peptides important in maintaining cardiovascular homeostasis. Distinct from the cardiac hormones ANP and BNP, CNP is expressed in a wide range of tissues including those of the central nervous system, reproductive system, skeleton and vascular endothelium. Regulation of endothelial CNP is still poorly understood but in vitro studies implicate a range of cytokines including TGF beta and other growth factors such as PDGFs and FGFs.

CNP acts locally and is rapidly degraded at the source, but products of CNP gene expression can be measured in plasma. Amino terminal propeptide of C-type natriuretic peptide (NTproCNP) in contrast is not rapidly degraded in the plasma and thus provides a new approach to measuring tissue CNP production in vivo (Prickett T C R et al. (2001) Biochemical and Biophysical Research Communications 286(3):513-517).

To the inventor's knowledge, there has only been one study where CNP and/or NTproCNP peptide levels have been examined in relation to endothelial function and vascular risk of development of arteriosclerosis. In that study of 117 older men selected in order to establish risk of vascular disease, lower concentrations of NTproCNP were associated with higher vascular risk scores and impaired endothelial function (Vlachopoulos C et al (2010) Atherosclerosis 211 (2):649-55). These findings were consistent with the view that lower CNP within the vasculature (reflected by lower concentrations of the peptide in plasma) predispose subjects to arteriosclerosis. In contrast, the present inventors have found that in contrast to the only earlier study, increase in plasma NTproCNP is in fact associated with vascular risk.

In addition, there has been no previous examination of the role of CNP concentration, and in particular NTproCNP concentration in the pregnancy setting and in particular in pregnant subjects which develop a vascular-related adverse event during pregnancy.

SUMMARY OF THE INVENTION

The present disclosure is based on the premise that NTproCNP is a biomarker of vascular disorders in subjects and furthermore it is a biomarker of predicting vascular-related adverse event risk in pregnant subjects. In particular, the present disclosure is based on the finding that a positive correlation exists between positive prediction of a vascular disorder event in a subject and the concentration of the circulating marker NTproCNP (also referred to as NT-CNP) in humans an animals. In addition, the present disclosure is based on the finding that there is also a positive correlation between the occurrence of a vascular-related adverse event during pregnancy and the concentration of the circulating marker NTproCNP in the maternal circulation.

In one embodiment, the present disclosure provides a method of predicting an adult subject's risk of acquiring a vascular disorder, comprising:

(i) measuring N-terminal pro-C-type natriuretic peptide (NTproCNP) in a biological sample from the subject, and (ii) comparing the measured level of NTproCNP against a reference interval from a suitable control population, wherein an increase in the circulating level of NTproCNP compared with the control population is predictive of increased risk of acquiring a vascular disorder, and further wherein said measuring step comprises detecting binding between NTproCNP and a binding agent that selectively binds to NTproCNP.

In one example, the method further comprises the step of (iii) administering a treatment regimen to the subject where the subject is found to have an increase in circulating NTproCNP compared with the level of circulating NTproCNP from the control population.

In a further example, the method further comprises measuring the level of NTproCNP in a first biological sample from the subject and measuring the level of NTproCNP in second biological sample, wherein the second biological sample is taken from the same subject as the first sample but at a later period in time, and comparing the levels of NTproCNP in said first and second samples, wherein an increase in the circulating level of NTproCNP between the first and second samples is indicative of increased risk of acquiring a vascular disorder.

In another embodiment, the present disclosure provides a method for diagnosing a vascular disorder in an adult subject comprising:

(i) measuring N-terminal pro-C-type natriuretic peptide (NTproCNP) in a biological sample from the subject, and (ii) comparing the measured level of NTproCNP against a reference interval from a suitable control population, wherein an increase in the circulating level of NTproCNP compared with the control population is indicative of a vascular disorder, and further wherein said measuring step comprises detecting binding between NTproCNP and a binding agent that selectively binds to NTproCNP.

In one example, the method further comprises the step of (iii) administering a treatment regimen to the subject where the subject is found to have an increase in circulating NTproCNP compared with the level of circulating NTproCNP from the control population.

In a further example according to any embodiment, measuring NTproCNP in a biological sample may occur more than once. For example, one, two, three, four, five, ten, fifteen etc measurements may be performed over a time period spanning hours, days, weeks, months or years.

In a further example, the method comprises measuring the level of NTproCNP in a first biological sample from the subject and measuring the level of NTproCNP in second biological sample, wherein the second biological sample is taken from the same subject as the first sample but at a later time point, and comparing the levels of NTproCNP in said first and second samples, wherein an increase in the circulating level of NTproCNP between the first and second samples is indicative of occurrence of a vascular disorder and/or persistence of a vascular disorder. Timing between first and second samples will typically be at the discretion of the clinician. This may be, for example, a period of minutes, hours, days, weeks, months or years.

In another embodiment, the present disclosure provides a method for diagnosing arteriosclerosis in an adult subject comprising:

(i) measuring N-terminal pro-C-type natriuretic peptide (NTproCNP) in a biological sample from the subject, and (ii) comparing the measured level of NTproCNP against a reference interval from a suitable control population, wherein an increase in the circulating level of NTproCNP compared with the control population is indicative of arteriosclerosis, and further wherein said measuring step comprises detecting binding between NTproCNP and a binding agent that selectively binds to NTproCNP.

In one example, the method further comprises the step of (iii) administering an arteriosclerosis treatment regimen to the subject where the subject is found to have an increase in circulating NTproCNP compared with the circulating NTproCNP in the control population.

A "suitable control population" according to the present disclosure refers to sex- and age-matched subjects for which the vascular information is known. The control population is used to provide a suitable reference interval by which the measured NT-CNP level is compared.

A "vascular disorder" according to the present disclosure may be selected from one or more of the following including Coronary Artery Disease (CAD), Acute Coronary Syndrome (ACS), unstable angina, myocardial infarction; Acute Coronary Ischaemic Syndrome, thrombotic Stroke; Transient Ischaemic Attack (TIA), Peripheral Artery Disease (PAD), Deep Vein thrombosis (DVT), arteriosclerosis, atherosclerosis, Atrial Fibrillation, catheter thrombotic occlusion; thrombotic occlusion and reocclusion, and arterial thrombosis of any vessel, and pregnancy-related vascular disorders.

In one example, the vascular disorder is coronary artery disease. In another example, the vascular disorder is arteriosclerosis. In another example, the vascular disorder is atherosclerosis.

In another embodiment, the present disclosure provides a method for predicting a pregnant subject's risk of acquiring a pregnancy-related vascular disorder, comprising:

(i) measuring N-terminal pro-C-type natriuretic peptide (NTproCNP) in a biological sample from the pregnant subject, and (ii) comparing the measured level of NTproCNP against a reference interval from a suitable control population of pregnant subjects;

wherein an increase in the measured circulating level of NTproCNP compared with reference interval from the control population is predictive of acquiring a pregnancy related vascular disorder, and further wherein said measuring step comprises detecting binding between NTproCNP and a binding agent that selectively binds to NTproCNP.

In a particular example, the method is strongly predictive of occurrence of a pregnancy related vascular disorder during pregnancy. In still a further example, the method predicts the occurrence of a pregnancy related vascular event with a positive predictive value of at least 78%, Expressed in another way, 78% of cases exhibiting an increased level of NTproCNP will experience a pregnancy related vascular event.

In a particular example, a pregnancy-related vascular disorder is an adverse event which may occur either in the pregnant female subject during pregnancy (gestation) or in the developing fetus. Such conditions according to the present disclosure may be selected from accelerated fetal growth, reduced fetal growth, fetal loss, placental abruption, pre-eclampsia (gestational hypertension), hypertension, preterm delivery (including spontaneous and threatened preterm delivery), ante partum haemorrhage, hyperglycaemia, umbilical vascular disorder, disorder of placental growth, and HELLP syndrome or combinations of any of these. In one example, a disorder of placental growth is intra uterine growth restriction (IUGR). In another example, a disorder of placental growth is villitis, ischaemia, or placental hypoperfusion.

Methods for assessing such adverse events will be known to persons skilled in the art. Such methodologies include ultrasound, doppler scanning, measurement of blood pressure blood testing, and/or amniocentesis.

A "control population of pregnant subjects" according to the present disclosure refers to age-matched subjects at the same period of gestation with uncomplicated/normal pregnancy. The control population is used to provide a suitable reference interval by which the measured NTproCNP level is compared. In one example, the control subjects do not suffer from one or more conditions selected from impaired renal function, chronic liver disease, metabolic bone disease or chronic heart disease since such conditions are implicated in artificially elevating the NTproCNP level.

In one example, measurement of NTproCNP is determined at 20-24 weeks gestation. In another example, measurement of NTproCNP is determined at 24 weeks gestation.

In one example, a NTproCNP plasma concentration >13.3 pmol/L is predictive of an adverse event occurrence in the subject.

In another embodiment, the present disclosure provides a method for predicting a pregnant subject's risk of acquiring a pregnancy-related vascular disorder, comprising:

(i) measuring N-terminal pro-C-type natriuretic peptide (NTproCNP) level in a biological sample from the pregnant subject at a first time point, and (ii) measuring NTproCNP level in a biological sample from the same subject at a second time point;

wherein an increase in the circulating level of NTproCNP between the first and second time points is predictive of a pregnancy-related vascular disorder, and further wherein said measuring step comprises detecting binding between NTproCNP and a binding agent that selectively binds to NTproCNP.

In a particular example, the pregnancy-related vascular disorder is an adverse event as described above.

In one example, the first time point is prior to 24 weeks gestation and the second time point is at or after 24 weeks gestation.

In another example, the first time point is about 20 weeks gestation and the second time period is about 24 weeks, 28 weeks, 32 weeks or 36 weeks gestation.

In yet another example, an increase of at least about 25-33 delta % (percentage change) in circulating NTproCNP level where first and second time points are four weeks apart is predictive of a pregnancy related vascular disorder or adverse event onset in the subject.

The term "delta %" as used herein is understood to refer to the percentage change in a given variable (i.e. the level or concentration of NTproCNP). The delta percentage is determined by taking the final concentration of NTproCNP and subtracting the initial concentration of NTproCNP and then dividing this value by the initial concentration of NTproCNP where the result is expressed as a percentage. Thus, by way of non-limiting example, an increase of 4 pmol/L from an initial NTproCNP concentration of 13 pmol/L represents a 31% change.

For the sake of clarity, an increase of at least about 25-33 delta % includes, for example, 25, 26, 27, 28, 29, 30, 31, 32, 33 delta percentage (% change), as well as fractions there between.

In yet another example, the method may further comprises measuring NTproCNP in a biological sample at a further time point(s). Preferably this comprises comparing the NTproCNP concentrations between samples at a 4 week interval wherein a difference of >4 pmol/L is predicative of an adverse event in the subject.

The term "measuring NTproCNP" in a biological sample refers to methodologies that enable the determination of NTproCNP peptide level or concentration in the sample. In one example, the NTproCNP concentration is expressed as pmol/L. In another example, the NTproCNP concentration is expressed as a percentage change (delta %). The terms NTproCNP concentration or NTproCNP level may be used interchangeably.

In one example according to any method of the disclosure, the biological sample is a body fluid. In another example, the body fluid is selected from plasma, blood, serum, urine, synovial fluid, cerebrospinal fluid, lymph, seminal fluid, amniotic fluid, vaginal secretions or any other body fluid. In a particular example, the biological sample is circulating plasma.

In another embodiment, the present disclosure also provides a method for predicting a non-pregnant subject's risk of acquiring a pregnancy related vascular disorder during pregnancy, comprising:

(i) measuring NTproCNP in a biological sample from the subject at a first time point before pregnancy;

(ii) measuring NTproCNP in a biological sample from the same subject at a second time point during pregnancy;

(iii) comparing the measured level of NTproCNP between the first and the second time point wherein a change in the circulating level of NT-CNP between the first and second time points is predicative of a pregnancy related vascular disorder during pregnancy, and further wherein said measuring step comprises detecting binding between NTproCNP and a binding agent that selectively binds to NTproCNP.

In one example, the absence of a significant decrease in circulating level or concentration between the first time point and a second time point measured at any point from 4 weeks up to 20 weeks gestation is predictive of a pregnancy related vascular disorder or adverse event in the subject. In a further example, the second time point may be taken at 8, 12, 16 or 20 weeks gestation, but does not exclude a sample point taken at 5, 6, 7, 9, 10, 11, 13, 14, 15, 17, 18 and/or 19 weeks gestation. In another example, the second time point corresponds with a pregnancy screening visit which is typically performed around 12 weeks gestation.

In another example, an increase in the circulating level of NTproCNP between the first and second time points is predictive of a pregnancy related vascular disorder. In one example, the second time point is at least 24 weeks gestation. In another example, the second time point is at least 28 weeks, 32 weeks or 36 weeks gestation.

In another example, the method may include measuring NTproCNP in one or more further time points during pregnancy. For example, one, two, three, four, five, seven, eight measurements may be performed over the pregnancy period. In a further example, a difference of >4 pmol/L between successive measurements separated by a period of four weeks is predictive of a pregnancy related vascular disorder. In another example, an increase of at least about 25-33 delta % (percentage change) in circulating NTproCNP level during gestation where first and second time points are four weeks apart is predictive of a pregnancy related vascular disorder or adverse event onset in the subject.

In a particular example, the pregnancy related vascular disorder is an adverse event as described above.

According to any method as described herein, the method may further comprise a step of administering an appropriate treatment regimen to the subject. In particular, the treatment regimen should be administered to the subject where the subject is found to have an increase in circulating plasma NTproCNP concentration compared with the circulating NTproCNP plasma concentration in the control population or there is an increase in plasma circulating NTproCNP concentration between a first and a second time point.

Appropriate treatment of subjects will be familiar to persons skilled in the art. Such treatment regimens may include administration of appropriate medication, for example anti-vascular agents are described below. Alternative treatment regimens may include bed rest or induction of fetal delivery.

In another embodiment, the present disclosure also provides a method for monitoring a pregnant subject for onset and/or progression of a pregnancy related vascular disorder, the method comprising:

(i) measuring the level of NTproCNP in a first biological sample from the subject;

(ii) measuring the level of NTproCNP in a second biological sample wherein the second biological sample is taken from the same subject as the first sample but at a later time point; and (iii) comparing the measured level of NTproCNP in said first and second samples, wherein an increase in the level of NTproCNP between the first and second samples is predictive of onset of a pregnancy related vascular disorder and/or progression of an existing pregnancy-related vascular disorder and wherein a decrease in the level of NTproCNP between the first and second samples is predictive of uncomplicated pregnancy and/or recovery/improvement in a pregnancy related vascular disorder.

In one example, the method further comprises, where the subject is found to have an increased level of NTproCNP between the first and second samples, administering to the subject an appropriate treatment regimen. In one example, the treatment regimen comprises treating the subject for gestational diabetes. In another example, the treatment regimen comprises treating the subject for pre eclampsia. In another example, the treatment regimen comprises treating the fetus. In one example treatment of the fetus comprises surgery.

In one example according to any method disclosed herein, the measuring step comprises detecting binding between NTproCNP and a binding agent that selectively binds NTproCNP. In one example, the binding agent is an antibody or antigen-binding fragment. In one example, the antibody is a monoclonal antibody or antigen-binding fragment. In one example, binding of NTproCNP is measured using antibodies or antigen-binding fragments that are immobilised to a solid phase.

In one example, the method for monitoring a pregnant subject for development of a pregnancy-related vascular disorder may comprises a further step of measuring the level of CNP in a biological sample from the subject. The present inventors have found that placental CNP and NTproCNP are increased in women with adverse events compared to those without adverse events during pregnancy. In one example, the sample is placental tissue, in another example, the sample is a chorionic villous sample (CVS). Alternatively, if a pregnant subject has been shown to have a high circulating NTproCNP, then a further CVS sample may be taken and the level of CNP measured which may alert the obstetrician to further tests or treatment that may be required or more frequent monitoring of the pregnant subject during pregnancy.

In one example according to any method of the disclosure, the subject is a human or non-human primate. In another example, the subject is a human. In one example, the subject may be undergoing a treatment regimen for a vascular disorder or pregnancy related vascular disorder. Where a significant deviation from the mean control level/reference interval is found, a clinician may amend the treatment regimen accordingly. For example, NTproCNP may serve as an index of the vascular effects of statin therapy. Statins (HMG-CoA reductase inhibitors) have been widely utilised in clinical practice to lower cholesterol which is implicated in the development of atherosclerosis. By monitoring the NTproCNP levels in the subject over time, any change in circulating levels of NTproCNP can be used by a clinician to adjust the dose and/or frequency of statin administered to the subject to treat the disorder.

In another embodiment, the present disclosure provides a method for monitoring the responsiveness of an adult subject to treatment with an anti-vascular agent or therapy, the method comprising:

(i) measuring the level of NTproCNP in a first biological sample from the subject;

(ii) measuring the level of NTproCNP in a second biological sample wherein the second biological sample is taken from the same subject; and (iii) comparing the measured levels of NTproCNP in said first and second samples, wherein an increase in the level of NTproCNP between the first and second samples is indicative of poor response to an anti-vascular agent or therapy and wherein a decrease in the level of NTproCNP between the first and second samples is indicative of good response to an anti-vascular agent or therapy.

The subject according to this embodiment may be a pregnant or a non-pregnant subject.

In one example, an increase of at least about 25-33 delta % (percentage change) in circulating NTproCNP level between first and second samples is indicative of poor response to anti-vascular therapy. In another example, a decrease of at least about 25-33 delta % (percentage change) in circulating NTproCNP level between first and second samples is indicative of good response to anti-vascular therapy. In another example, the first and second samples are taken 4 weeks apart.

In one example, the method further comprises, increasing or decreasing the dose and/or frequency of anti-vascular therapy administered to the subject depending upon the corresponding increase or decrease in the circulating level of NTproCNP.

In one example, the first sample is taken prior to administration of any anti-vascular agent or combination thereof and the second sample taken after administration of any anti-vascular agent or combination thereof. In another example, the first and second samples are taken following administration of any anti-vascular agent or combination thereof. The taking of the first and second samples and measurement of NTproCNP will typically be at the discretion of the clinician. The period between taking the samples may also be at the discretion of the clinician and may be, for example, a period of minutes, hours, days, weeks, months or years depending on the anti-vascular therapy that is administered to the subject.

In one example, the anti-vascular agent or therapy is selected from, but not limited to, HMG-CoA reductase inhibitors, antihyperlipidemic agents, endothelial growth factor agents (e.g. anti-VEGF antibodies such as bevacizumab), anti-microtubule agents (e.g. vinblasine, paclitaxel, BTO-956), ultrasound (as described in WO 08/042855), fusion polypeptides (as described in U.S. Pat. No. 7,618,943), indole-containing compounds (as described in WO 04/099139), angioplasty, stents, anticoagulants, angiotensin-converting enzyme inhibitors (ACE inhibitors), phosphodiesterase inhibitors (PDE inhibitors) beta blockers, nitrates, angiotensin II receptor blockers (ARBs), calcium channel blockers (CCBs), alpha blockers, alpha-beta blockers, vasodilator, or any combination thereof.

Depending on whether the subject is pregnant, the type of anti-vascular agent or therapy administered will be at the discretion of the clinician. For example, in a pregnant subject, the therapy may be administered in order to augment blood flow to the uterus. For example, the subject may be administered a PDEv inhibitor such as Viagra or Cialis or a CNP agonist. Thus, in another embodiment, the present disclosure also provides a method for monitoring the requirement for, or responsiveness of an adult subject to treatment with a PDEv inhibitor or a CNP agonist.

In another embodiment, the present disclosure provides a kit for measuring the level of NTproCNP in a biological sample obtained from a subject with, or at risk of, acquiring a vascular disorder, including a pregnancy-related vascular disorder, comprising a binding agent that selectively binds to NTproCNP and which can be quantitatively measured upon binding to NTproCNP. The kit may be used for measurement of NTproCNP levels in both pregnant and non-pregnant subjects. In another example, the subject is an adult subject.

In one example, the biological sample obtained from the subject is selected from blood, plasma, serum, urine, synovial fluid, cerebrospinal fluid, lymph, seminal fluid, vaginal secretions, amniotic fluid or any other body fluid.

In one example, the binding agent is measured by chromatography, oxidation/reduction, fluorescence, luminescence, mass, molecular weight, radioactivity or any combination thereof.

The present disclosure also provides an NTproCNP binding agent that selectively binds NTproCNP for use in predicting an adult subject's risk of acquiring a vascular disorder.

The present invention also provides an NTproCNP binding agent that selectively binds NTproCNP for use in diagnosing a vascular disorder in an adult subject.

The present invention also provides an NTproCNP binding agent that selectively binds NTproCNP for use in monitoring the responsiveness of an adult subject to treatment with an anti-vascular agent.

The present invention also provides an NTproCNP binding agent that selectively binds NTproCNP for use in predicting a pregnant subject's risk of acquiring a pregnancy related vascular disorder.

The present invention also provides NTproCNP binding agent that selectively binds NTproCNP for use in monitoring a pregnant subject for development of a pregnancy related vascular disorder.

The present invention also provides use of an NTproCNP binding agent in the manufacture of a medicament for predicting an adult subject's risk of acquiring a vascular disorder.

The present invention also provides use of an NTproCNP binding agent in the manufacture of a medicament for diagnosing a vascular disorder in an adult subject.

The present invention also provides use of an NTproCNP binding agent in the manufacture of a medicament for monitoring the responsiveness of an adult subject to treatment with an anti-vascular agent.

The present invention also provides use of an NTproCNP binding agent in the manufacture of a medicament for predicting a pregnant subject's risk of acquiring a pregnancy related vascular disorder.

The present invention also provides use of an NTproCNP binding agent in the manufacture of a medicament for use in monitoring a pregnant subject for development of a pregnancy related vascular disorder.

DETAILED DESCRIPTION

General

Figure 1:
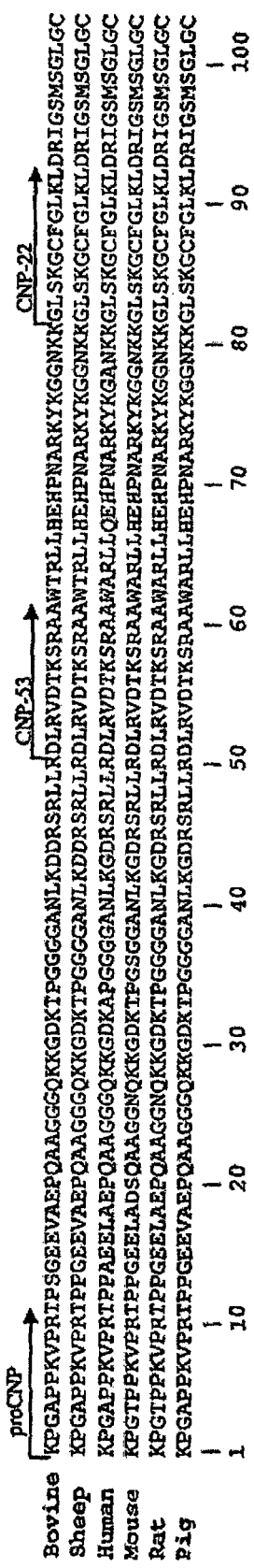
FIG. 1 shows the published amino acid sequences predicted for proCNP from gene/cDNA sequencing studies. The sequences for bovine, sheep, human, mouse, rat and pig proCNP sequences are aligned.

The term "and/or", e.g., "X and/or Y" shall be understood to mean either "X and Y" or "X or Y" and shall be taken to provide explicit support for both meanings or for either meaning.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations or any two or more of said steps or features.

The present invention is not to be limited in scope by the specific embodiments described herein, which are intended for the purpose of exemplification only. Functionally-equivalent products, compositions and methods are clearly within the scope of the invention, as described herein.

Any embodiment herein shall be taken to apply mutatis mutandis to any other embodiment unless specifically stated otherwise.

Unless specifically defined otherwise, all technical and scientific terms used herein shall be taken to have the same meaning as commonly understood by one of ordinary skill in the art (for example, in immunology, immunohistochemistry, protein chemistry, and biochemistry).

Unless otherwise indicated, techniques utilized in the present disclosure are standard procedures, well known to those skilled in the art. Such techniques are described and explained throughout the literature in sources such as, J. Sambrook et al., Molecular Cloning: A Laboratory Manual, Cold Spring Harbor Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al., (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbor Laboratory, (1988), and J. E. Coligan et al., (editors) Current Protocols in Immunology, John Wiley & Sons (including all updates until present).

Selected Definitions

The term "adult" subject as used herein is defined by skeletal age, that is, it is intended to refer to a subject whose linear growth has ceased. In one example, an adult subject is of a biological age ≥20 years.

The term "biological sample" as used herein includes biological fluids selected from plasma, blood, serum, urine, synovial fluid, cerebrospinal fluid, lymph, seminal fluid, amniotic fluid, vaginal secretions or any other body fluid.

The term "level" as used herein is intended to refer to the amount per weight or weight per weight of NT-CNP. It is also intended to encompass "concentration" expressed as amount per volume or weight per volume. The term "circulating level" is intended to refer to the amount per weight or weight per weight or concentration of NT-CNP present in the circulating fluid. Typically, the concentration of NTproCNP is expressed as pmol/L.

The term "CNP" as used herein refers to C-type natriuretic peptide, and refers to biologically active peptides derived from the prohormone (proCNP(1-103) that is the product of the CNP gene NPPC. The known biologically active peptides include CNP-53 (proCNP(51-103) and CNP-22 (proCNP(82-103)). In one example, the CNP is human CNP.

The term "NTproCNP" as used herein is intended to refer to the amino terminal pro C-type natriuretic peptide. It encompasses any discriminatingly detectable sequence of consecutive amino acids selected from the amino acid sequence present in proCNP(1-81). The term can be used interchangeably with NTproCNP. In one example, the NTproCNP is human NTproCNP.

The term "reference interval" as used herein is intended to refer to a figure within a statistical band of a representative concentration or alternatively a figure with an upper or lower concentration. The reference interval will typically be obtained from subjects that do not have any pre-existing conditions that could result in artificially elevating the level of circulating NT-CNP. These conditions are discussed elsewhere herein. The term reference interval may also refer to the mean NTproCNP concentration from a sample of control subjects.

The term "subject" as used herein is intended to refer to a human or non-human primate. In one example, the subject is a human. In another example, the subject is a pregnant human subject.

The term "pregnant" as used herein refers to the state of pregnancy which is the fertilization and development of offspring (embryo or fetus) in a women's uterus.

The term "gestation" refers to the period of development of an embryo or fetus in the uterus from conception until birth. In humans the period of gestation is about 266 days (about 38-40 weeks).

The term "binding agent" as used herein is intended to refer to any molecule that binds NTproCNP peptides, including small molecules, antibodies from any species whether polyclonal or monoclonal, antigen-binding fragments such as Fab and Fab2, humanized antibodies, chimeric antibodies, or antibodies modified in other ways including substitution of amino acids, and/or fusion with other peptides or proteins (e.g. PEG). It also includes receptors or binding proteins from any species or modified forms of them. In one example, the binding agent specifically binds to NTproCNP.

The term "specifically binds" as used herein shall be taken to mean that the binding agent reacts or associates more frequently, more rapidly, with greater duration and/or with greater affinity to a particular substance than it does with alternative substances. For example, a binding agent that specifically binds to NTproCNP binds that protein or an epitope or immunogenic fragment thereof with greater affinity, avidity, more readily, and/or with greater duration than it binds to unrelated protein and/or epitopes or immunogenic fragments thereof. It is also understood by reading this definition that, for example, a binding agent that specifically binds to a first target (e.g. NTproCNP) may or may not specifically bind to a second target. As such, "specific binding" does not necessarily require exclusive binding or non-detectable binding of another molecule. Generally, but not necessarily, reference to binding means specific binding.

The term "vascular disorder" according to the present disclosure refers to a pathology of, or about the vasculature of the circulatory system. Exemplary conditions include Coronary Artery Disease (CAD); Acute Coronary Syndrome (ACS), including unstable angina and non-ST-elevated myocardial infarction; Acute Coronary Ischaemic Syndrome; first or subsequent thrombotic Stroke; Transient Ischaemic Attack (TIA); Peripheral Artery Disease (PAD); Deep Vein thrombosis (DVT); arteriosclerosis; atheroma, Atrial Fibrillation; catheter thrombotic occlusion; thrombotic occlusion and reocclusion; and arterial thrombosis of any vessel, including one or more of these.

The term "atheroma" as used herein is intended to refer to an accumulation and swelling in an artery wall which is usually made up of macrophage cells and/or cellular debris, and contains lipids (e.g. cholesterol), calcium and fibrous connective tissue. Atheroma occurs in atherosclerosis which is one of the three subtypes of arteriosclerosis, being atherosclerosis, Monckeberg's arteriosclerosis and arteriolosclerosis.

The term "atherosclerosis" as used herein refers to a chronic vascular inflammatory disease affecting arterial blood vessels. It is a response in large part due to the deposition of lipoprotein plaques (comprises of plasma proteins, cholesterol, triglycerides, calcium and scar tissue) on the walls of arteries.

The term "arteriosclerosis" as used herein refers to the general term describing any hardening (and loss of elasticity) of medium or large arteries. The term was known in the past as "myoconditis".

The term "coronary artery disease" as used herein refers to atherosclerosis of one or more of the coronary arteries.

The term "heart attack (myocardial infarction, AMI, MI)" is intended to refer to a medical condition where the blood supply to a part of the heart is interrupted, most commonly due to rupture of a vulnerable plaque in a coronary artery. A heart attack may also occur when a coronary artery temporarily contracts or goes into a severe spasm, effectively shutting off the flow of blood to the heart. In either case, the resulting ischemia or oxygen shortage causes damage and potential death of heart tissue.

A "thrombotic or thromboembolic event" as used herein is intended to include the following: atrial fibrillation, acute coronary syndrome including unstable angina, acute myocardial infarction ischaemic stroke, acute coronary ischaemic syndrome, thrombosis, thromboembolism, peripheral artery disease, deep vein thrombosis, arterial thrombosis of any vessel, catheter thrombotic occlusion, thrombotic occlusion and reocclusion, transient ischaemic attack, first or subsequent thrombotic stroke.

The term "TIA or Transient ischaemic attack" also known as a "mini-stroke" is intended to refer to a temporary interruption of blood flow to the brain. The symptoms (warning signs) are similar to an ischaemic stroke except they go away within a few minutes or hours. A TIA is an important indicator of full blown stroke risk, however, subjects frequently have a TIA without even knowing it.

The term "antibody" refers to an immunoglobulin molecule capable of specifically binding to a target, such as NT-CNP by virtue of an antigen binding site contained within at least one variable region. This term includes four chain antibodies (e.g., two light chains and two heavy chains), recombinant or modified antibodies (e.g., chimeric antibodies, humanized antibodies, primatized antibodies, de-immunized antibodies, half antibodies, bispecific antibodies) and single domain antibodies such as domain antibodies and heavy chain only antibodies (e.g., camelid antibodies or cartilaginous fish immunoglobulin new antigen receptors (IgNARs)). An antibody generally comprises constant domains, which can be arranged into a constant region or constant fragment or fragment crystallisable (Fc). Preferred forms of antibodies comprise a four-chain structure as their basic unit. Full-length antibodies comprise two heavy chains (~50-70 kDa) covalently linked and two light chains (~23 kDa each). A light chain generally comprises a variable region and a constant domain and in mammals is either a K light chain or a λ light chain. A heavy chain generally comprises a variable region and one or two constant domain(s) linked by a hinge region to additional constant domain(s). Heavy chains of mammals are of one of the following types α, δ, ε, γ, or μ. Each light chain is also covalently linked to one of the heavy chains. For example, the two heavy chains and the heavy and light chains are held together by inter-chain disulfide bonds and by non-covalent interactions. The number of inter-chain disulfide bonds can vary among different types of antibodies. Each chain has an N-terminal variable region ($V_H$ or $V_L$ wherein each are ~110 amino acids in length) and one or more constant domains at the C-terminus. The constant domain of the light chain ($C_L$ which is ~110 amino acids in length) is aligned with and disulfide bonded to the first constant domain of the heavy chain ($C_H$ which is ~330-440 amino acids in length). The light chain variable region is aligned with the variable region of the heavy chain. The antibody heavy chain can comprise 2 or more additional $C_H$ domains (such as, $C_H2$, $C_H3$ and the like) and can comprise a hinge region can be identified between the $C_H1$ and Cm constant domains. Antibodies can be of any type (e.g., IgG, IgE, IgM, IgD, IgA, and IgY), class (e.g., $IgG_1$, $IgG_2$, $IgG_3$, $IgG_4$, $IgA_1$ and $IgA_2$) or subclass. In one example, the antibody is a murine (mouse or rat) antibody or a primate (preferably human) antibody. The term "antibody" encompasses not only intact polyclonal or monoclonal antibodies, but also variants, fusion proteins comprising an antibody portion with an antigen binding site, humanised antibodies, human antibodies, chimeric antibodies, primatised antibodies, de-immunised antibodies or veneered antibodies.

The term "antigen binding fragment" shall be taken to mean any fragment of an antibody that retains the ability to bind to NT-CNP preferably specifically binds to NT-CNP. This term includes a Fab fragment, a Fab' fragment, a F(ab') fragment, a single chain antibody (SCA or SCAB) amongst others. An "Fab fragment" consists of a monovalent antigen-binding fragment of an antibody molecule, and can be produced by digestion of a whole antibody molecule with the enzyme papain, to yield a fragment consisting of an intact light chain and a portion of a heavy chain. An "Fab' fragment" of an antibody molecule can be obtained by treating a whole antibody molecule with pepsin, followed by reduction, to yield a molecule consisting of an intact light chain and a portion of a heavy chain. Two Fab' fragments are obtained per antibody molecule treated in this manner. An "F(ab')2 fragment" of an antibody consists of a dimer of two Fab' fragments held together by two disulfide bonds, and is obtained by treating a whole antibody molecule with the enzyme pepsin, without subsequent reduction. A $(Fab')_2$ fragment. An "Fv fragment" is a genetically engineered fragment containing the variable region of a light chain and the variable region of a heavy chain expressed as two chains. A "single chain antibody" (SCA) is a genetically engineered single chain molecule containing the variable region of a light chain and the variable region of a heavy chain, linked by a suitable, flexible polypeptide linker.

C-Type Natriuretic Peptide Precursor

Natriuretic peptide precursor C (preproCNP), the protein coded by the gene NPPC, is cleaved to the 22 amino acid C-type natriuretic peptide (CNP), as well as proCNP and NTproCNP. Natriuretic peptide comprises a family of 3 structurally related molecules, atrial natriuretic peptide (ANP), brain natriuretic peptide (BNP) and C-type natriuretic peptide (CNP).

CNP has been shown to play an important role in regulating linear growth (see for example U.S. Pat. No. 7,919, 255 to the present inventors). It is produced in the growth plate and is expressed in a variety of tissues including vascular endothelium, heart tissue, circulating blood elements, stomach and reproductive tissues. Unfortunately, in healthy subjects there is virtually no detectable CNP present in circulation once linear growth has ceased as it is effectively sequestered and/or metabolised by cells. Therefore detection of CNP if at all possible, is close to the detection limit of most current analytical methods.

CNP is synthesised as a precursor protein that undergoes proteolytic processing before release from the cell. The amino terminal propeptide of CNP (NTproCNP) is a cleavage product of proCNP and is produced in equimolar amounts with CNP. NTproCNP was discovered and characterised by the present inventors (Prickett T C R et al (2001) Biochemical and Biophysical Research Communications vol 286(3):513-517). The level of NTproCNP in blood likely reflects the rate of CNP biosynthesis.

Plasma concentrations of NTproCNP are affected by renal clearance and/or metabolism. Increased concentrations are observed in adults when renal function falls below 30% of normal. Interpretation of NT-CNP levels in subjects with moderate or severe renal failure may therefore provide results that are artificially increased. Thus, it would be appropriate for the clinician to determine whether the subject has any pre-existing renal failure. In such subjects, it may be appropriate for the clinician to apply a correction factor which can be determined, for example by measuring serum creatinine (a commonly used indicator of renal function). Thus the clinician could determine a correction factor which is based on the ratio of NTproCNP to creatinine. Since the relation between the concentration of NTproCNP and creatinine is known in normal adult subjects, it is possible to determine a reference range for the ratio (NT CNP/creatinine) based on age and gender and use this to determine vascular risk in a subject.

Plasma concentrations of NTproCNP are also affected by liver cirrhosis and chronic liver diseases. A study of 193 patients with chronic liver diseases found that elevated NTproCNP levels indicated adverse prognosis (Koch A et al (2012) Clin Biochem 45(6):429-35. Thus, it would be appropriate for the clinician to determine whether the subject has any pre-existing chronic liver disease.

Plasma concentrations of NTproCNP are also affected by metabolic bone disease, particularly where the metabolic bone disease is manifested by increased bone turnover. In subjects with a pre-existing metabolic bone disorder, their level of NTproCNP may be artificially increased.

Plasma concentrations of NTproCNP are also affected by severe heart disease (ischaemic heart disease or congestive heart failure). In such subjects with pre-existing heart disease, their level of NTproCNP may be artificially increased.

Ideally, before assessing the subject the clinician would need to take a thorough history of the subject which may include checking for one or more of the above disorders (renal function, liver function, heart function, bone conditions). Where a subject is found to be suffering from one or more of the above disorders, the disorder should ideally be addressed before conducting any of the methods of the disclosure. For example, many renal disorders are treatable to obtain normal renal function. The NTproCNP concentrations are also expected to normalise within days of normalising the renal function in a subject so that the methods of the present invention are expected to provide more accurate results than before normalisation of the renal disorder. Alternatively, the clinician can apply a correction factor as discussed above.

Binding Agents to NTproCNP

NTproCNP is measured in a body fluid sample by detecting binding between NTproCNP and a binding agent that selectively binds NTproCNP. Binding agents for use in the methods of the present disclosure preferably have low cross-reactivity, for example with ANP and BNP. The binding agents may include antibodies or antigen-binding fragments such as Fab and F(ab)2, prepared using antigenic NTproCNP peptides or fragments thereof as immunising antigens. The polypeptide or fragments may also be coupled to a carrier as described. In one example, the binding agent is an antibody. The antibody may be a monoclonal or polyclonal antibody. Methods for producing polyclonal and monoclonal antibodies as well as fragments thereof are well known in the art (for example see Harlow and Lane, Antibodies: A Laboratory Manual, Cold Spring Harbor Laboratory, New York 1988). For reasons of specificity, monoclonal antibodies are currently preferred. It will be appreciated that humanised antibodies are not required for in vitro assays Commercial antibodies to NT-CNP and/or kits for assaying NT-CNP may also be used in the methods of the present disclosure. Suitable examples of such commercial antibodies include polyclonal sheep anti NT-CNP which is provided in kit form (Biomedica Gruppe), pro C-type natriuretic peptide (ProCNP) EIISA kit from antibodies online (catalog no. ABIN418357), antibodies and kits from Gentaur Molecular Products, and antibodies available from epitomics or invitrogen. Persons skilled in the art will be familiar with sourcing and obtaining commercially available antibodies.

In one example, the antibody is raised against an antigenic NTproCNP peptide. In one example, the antigenic NTproCNP peptide comprises a partial consecutive sequence of proCNP(1-81) of a suitable size to enable antibodies and other immuno-molecules to be raised against the peptide. In another example, the antigenic NTproCNP peptide comprises at least six consecutive amino acids from proCNP(1-81). This generally provides a sufficient epitope for specific amino acid detection. However, in some cases, it may be necessary to have at least eight amino acids to provide sufficient specificity for the peptide detection process.

In another example, at least 15 consecutive amino acids from proCNP(1-81) is employed. For the best ability to raise antibodies, proCNP(1-81) can be employed itself. Other examples of peptides that could be used in raising antibodies include proCNP(1-50), proCNP(1-81), and proCNP(51-81). proCNP(1-103) can also be used in certain circumstances as antibodies raised may cross-react with proCNP(1-81) and proCNP(1-50) peptides. The peptides useful in the present invention are collectively referred to as NTproCNP in this disclosure. The present disclosure also includes the use of functionally equivalent variants of the NTproCNP peptides.

The full length amino acid sequence of human proCNP (1-103) and other known mammalian proCNP sequences are shown in FIG. 1.

In another example, the antigenic NTproCNP peptide comprises NT-CNP(1-50), which the inventors have demonstrated is a major NT-CNP peptide circulating in humans, or a functional fragment or metabolite thereof. proCNP(1-81) and proCNP(51-81) and their metabolites are also useful. It is likely that circulating NTproCNP levels or concentrations are reflective of CNP levels in bodily tissues and fluids.

In another example, the antigenic peptide comprises proCNP(3-15). In another example, the antigenic peptide comprises proCNP(15-32), proCNP(26-42) or proCNP(38-50).

Monoclonal antibodies may be produced by known art methods. These include the immunological method described by Kohler et al (1975) Nature 256(5517):495-7 as well as the recombination DNA method described by Huse et al (1989) 246(4935):1275-81. The use of recombinant phage antibody systems to produce single chain variable antibody fragments, and subsequent mutation (such as site specific mutagenesis) or chain shifting to produce antibodies to NTproCNP peptides is also contemplated.

Conventional procedures for generating polyclonal antibodies are detailed in Harlow and Lane (supra). Briefly, the protocol requires immunisation of a selected animal host such as a rabbit, goat, donkey, sheep, rat or mouse (usually a rabbit), with an isolated NTproCNP peptide on a number of spaced occasions, with one or more test bleeds preceding exsanguination and blood collection. Serum may be separated from clotted blood by centrifugation. Serum may be tested for the presence of polyclonal antibodies using ELISA or radioimmunoassay competitive assays or art equivalent methods.

Antibodies specific to proCNP(1-15), proCNP(36-50) and proCNP(67-81) can be raised after first conjugating these or similar peptides to a large protein such as bovine serum albumin or bovine thyroglobulin to make them immunogenic. Coupling can be effected by use of any protein crosslinking agent including for example the common agents glutaraldehyde, carbodiimide or N-(e-maleimidocaproyloxy) succinimide ester (MCS)-providing a cysteine residue is added to the peptide sequence prior to coupling. Injection of these conjugates into rabbits, sheep, mice or other species at monthly intervals followed by collection of blood samples two weeks later will enable production of polyclonal antibodies or monoclonal antibodies from the spleens of mice.

For example, the mouse host described above may be sacrificed and its spleen removed. The messenger RNA (mRNA) are then isolated and cDNA made from the mRNA using specific primers for the heavy and light chains of the variable region of the antibodies and the polymerase chain reaction (PCR) amplification. The DNA sequences for the heavy and light chains are joined with a linker sequence, to ensure the correct reading frame. Then the DNA construct is inserted into a vector, for example, a plasmid or bacteriophage, or virus, for transformation into a host. In one example the vector is a bacteriophage.

Suitable hosts may be selected from prokaryotic, yeast, insect or mammalian cells. In one example, a prokaryotic host, preferably *Escherichia coli* is used. The bacteriophage produces a viral coat and the antibody fragments are expressed on the coat, a phage display library. The phage display library can be screened for antibody fragments with the appropriate affinity for the specific antigens. The library can be screened many times and modifications can be made to the antibody construct through protein engineering techniques, such as site directed mutagenesis and chain shuffling all of which are within the capabilities of the person skilled in the art.

Detection of Binding Agents

The present disclosure includes use of a detection system involving the binding of NTproCNP to a binding agent and then detecting the amount of bound agent. A similar solution is to detect the amount of unbound binding agent in a sample to get an indication of unbound or bound NTproCNP. It is intended that such alternative methods fall within the scope of the present disclosure as functional alternatives to directly detecting the amount of bound binding agent. Persons skilled in the art will appreciate that the concentration of NTproCNP in a sample can be readily calculated from the amount of NTproCNP in a sample when the sample volume is known.

The antibodies useful in the present disclosure are particularly useful in immunoassays for determining the presence and/or amount of NTproCNP in a sample. Due to variable binding affinities of different antibodies, the person skilled in the art will appreciate that a standard binding curve of measured values versus amount of NTproCNP in a sample should be established for a particular antibody to enable the amount of NTproCNP in a sample to be determined. Such a curve is used to determine the true amount of NTproCNP in a sample. In other words, a reference interval needs to be determined for each binding agent used.

Sample materials include cells, cell membranes and biological fluids but are not limited thereto. In terms of the present disclosure, usually a biological fluid is selected from whole blood, plasma, serum or urine. In one example, the sample is tested in vitro.

Immunoassays specific for NTproCNP peptides require the production of antibodies that specifically bind to NTproCNP peptides. In one example, the antibody recognizes amino acids within proCNP(1-15) In another example, the antibody recognised amino acids within proCNP(3-15). These antibodies, while being specific for NTproCNP peptides have broad NTproCNP specificity. Antibodies useful in the invention bind to one or more of the four peptides proCNP (1-50), proCNP(1-81), proCNP (51-81) and proCNP (1-103) or their metabolites. The antibodies can be used to construct immunoassays with broad specificity, as in competitive binding assays below, or used in conjunction with other antibodies described below in sandwich type assays to produce assays specific to each of the three peptides or to other NTproCNP peptides. The person skilled in the art will appreciate that non-competitive assays are also possible. The latter antibodies for sandwich immunoassays include those specific for amino acid sequences within proCNP(1-15), proCNP(36-50), proCNP(67-81), proCNP (15-32), proCNP(26-42) or proCNP(10-21).

The methods of the present disclosure can be performed using a kit as provided herein. A kit for measuring the level of NTproCNP in a biological sample is provided. The kit comprises a binding agent that selectively binds to NTproCNP and which can be quantitatively measured upon binding to NTproCNP. Binding agents are as described above.

In another example, indicators may also be used. Indicators may be employed in ELISA and RIA methods.

Polyclonal and monoclonal antibodies can be used in competitive binding or sandwich type assays. In one example of this method a liquid sample is contacted with the antibody and simultaneously or sequentially contacted with a labelled NTproCNP peptide or modified peptide containing the epitope recognised by the antibody.

The label can be a radioactive component such as $^{125}$I, $^{131}$I, $^{3}$H, $^{14}$C or a nonradioactive component that can be measured by time resolved fluorescence, fluorescence, fluorescence polarisation, luminescence, chemiluminescence or colorimetric methods. These compounds include europium or other actinide elements, acrinidium esters, fluorescein, or radioactive material such as those above, that can be directly measured by radioactive counting, measuring luminescent or fluorescent light output, light absorbance etc. The label can also be any component that can be indirectly measured such as biotin, digoxin, or enzymes such as horseradish peroxidase, alkaline phosphatase. These labels can be indirectly measured in a multitude of ways. Horseradish peroxidase for example can be incubated with substrates such as o-Phenylenediamine Dihyhdrochloride (OPD) and peroxide to generate a coloured product whose absorbance can be measured, or with luminol and peroxide to give chemiluminescent light which can be measured in a luminometer. Biotin or digoxin can be reacted with binding agents that bind strongly to them; e.g. avidin will bind strongly to biotin. These binding agents can in turn be covalently bound or linked to measurable labels such as horseradish peroxidase or other directly or indirectly measured labels as above. These labels and those above may be attached to the peptide or protein: —during synthesis, by direct reaction with the label, or through the use of commonly available crosslinking agents such as MCS and carbodiimide, or by addition of chelating agents.

Following contact with the antibody, usually for 18 to 25 hours at 4° C., or 1 to 240 minutes at 30° C. to 40° C., the labelled peptide bound to the binding agent (antibody) is separated from the unbound labelled peptide. In solution phase assays, the separation may be accomplished by addition of an anti gamma globulin antibody (second-antibody) coupled to solid phase particles such as cellulose, or magnetic material. The second-antibody is raised in a different species to that used for the primary antibody and binds the primary antibody. All primary antibodies are therefore bound to the solid phase via the second antibody. This complex is removed from solution by centrifugation or magnetic attraction and the bound labelled peptide measured using the label bound to it. Other options for separating bound from free label include formation of immune complexes, which precipitate from solution, precipitation of the antibodies by polyethyleneglycol or binding free labelled peptide to charcoal and removal from solution by centrifugation of filtration. The label in the separated bound or free phase is measured by an appropriate method such as those presented above.

Competitive binding assays can also be configured as solid phase assays that are easier to perform and are therefore preferable to those above. This type of assay uses plates with wells (commonly known as ELISA or immunoassay plates), solid beads or the surfaces of tubes. The primary antibody is either adsorbed or covalently bound to the surface of the plate, bead or tube, or is bound indirectly through a second anti gamma globulin or anti Fc region antibody adsorbed or covalently bound to the plate. Sample and labelled peptide (as above) are added to the plate either together or sequentially and incubated under conditions allowing competition for antibody binding between NTproCNP in the sample and the labelled peptide. Unbound labelled peptide can subsequently be aspirated off and the plate rinsed leaving the antibody bound labelled peptide attached to the plate. The labelled peptide can then be measured using techniques described above.

Sandwich type assays are more preferred for reasons of specificity, speed and greater measuring range. In this type of assay an excess of the primary antibody to NTproCNP is attached to the well of an ELISA plate, bead or tube via adsorption, covalent coupling, or an anti Fc or gamma globulin antibody, as described above for solid phase competition binding assays. Sample fluid or extract is contacted with the antibody attached to the solid phase. Because the antibody is in excess this binding reaction is usually rapid. A second antibody to NTproCNP is also incubated with the sample either simultaneously or sequentially with the primary antibody. This second antibody is chosen to bind to a site on NTproCNP that is different from the binding site of the primary antibody. These two antibody reactions result in a sandwich with the NTproCNP from the sample sandwiched between the two antibodies. The second antibody is usually labelled with a readily measurable compound as detailed above for competitive binding assays. Alternatively a labelled third antibody which binds specifically to the second antibody may be contacted with the sample. After washing the unbound material the bound labelled antibody can be measured by methods outlined for competitive binding assays. After washing away the unbound labelled antibody, the bound label can be quantified as outlined for competitive binding assays.

A dipstick type assay may also be used. These assays are well known in the art. They may for example, employ small particles such as gold or coloured latex particles with specific antibodies attached. The liquid sample to be measured may be added to one end of a membrane or paper strip preloaded with the particles and allowed to migrate along the strip. Binding of the antigen in the sample to the particles modifies the ability of the particles to bind to trapping sites, which contain binding agents for the particles such as antigens or antibodies, further along the strip. Accumulation of the coloured particles at these sites results in colour development are dependent on the concentration of competing antigen in the sample. Other dipstick methods may employ antibodies covalently bound to paper or membrane strips to trap antigen in the sample. Subsequent reactions employing second antibodies coupled to enzymes such as horse radish peroxidase and incubation with substrates to produce colour, fluorescent or chemiluminescent light output will enable quantitation of antigen in the sample.

In one example, an antibody with specificity to proCNP (1-15) is used. In another example, an antibody with specificity to proCNP(3-15) is used.

Applications of NTproCNP in Vascular Disorders

The use of NTproCNP and binding agents described herein in assays for the prognosis or diagnosis of vascular disorders are of significance in detecting early onset of, for example coronary heart disease or pregnancy related vascular disorders and adverse events. The methods provide the clinician with the ability to stratify subjects who may be potentially at risk of a vascular disorder or worsening of an existing vascular disorder. Additionally, the methods of the present disclosure provide the clinician with a means to monitor a subject's responsiveness to their existing therapy. For example, by measuring the NTproCNP levels in a subject over time, the clinician can monitor a subject's response to statin therapy or treatment with thrombolytic agents. Additionally, with regard to pregnant subjects, the methods disclosed herein provide a means for determining which subjects are at risk of acquiring a vascular related disorder during pregnancy and thus require more frequent monitoring by their obstetrician.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

Methods and Subject Criteria

Healthy Volunteer Subjects

Participants were healthy adults (n=242), aged 21-80 yr, recruited from the electoral rolls of Canterbury, New Zealand. Results from measurements of CNP forms in 16 healthy adults, studied for the purpose of defining a tentative normal range for these analytes, were also added to the data set (total 258).

Subjects with a history of renal disorder, ischaemic heart disease (IHD) and or congestive heart failure (CHF) were excluded. Long term drug ingestion included non-steroidal anti-inflammatories, analgesics, hypotensives, lipid lowering drugs, anti-depressants and proton pump inhibitors. Of the 258 subjects studied, 110 were taking no medication. The study was approved by the New Zealand Upper South B Regional Ethics Committee and informed consent was given by all participants prior to enrolment.

At the time of blood sampling, self-reported medical and family history, and details of current medication were recorded. A subject's vascular risk score was calculated by totaling the number of risk factors defined here as: history of smoking, hypertension or lipid disorder. Height and body weight were measured. A sample of venous blood was then drawn into EDTA collection tubes (Becton-Dickinson, Plymouth, UK), and placed in an ice water slurry and centrifuged (2800 g for 10 min) within 10 min of collection. The aspirated plasma was then stored at minus 80° C. until measurement of CNP and NTproCNP and creatinine.

Coronary Artery Disease Subjects

Patients admitted to either Christchurch Hospital or Auckland City Hospital were recruited using the following inclusion criteria: ischemic chest discomfort plus one or more of 1) ECG changes (ST segment depression or elevation of at least 0.5 mm, T-wave inversion of at least 3 mm in at least 3 leads, or left bundle branch block), 2) elevated levels of cardiac markers, 3) a history of coronary disease, or 4) age of at least 65 years in patients with diabetes or vascular disease. Patients were excluded if they had a severe co-morbidity that limited their life expectancy to less than 3 years. Anthropometric and clinical characteristics, as well as clinical events were recorded at planned follow-up clinic visits, from questionnaires, patient notes and National Health Information Services and hospital Patient Management System databases. Patients were followed for a median of 2.8 years (0.1-6.9 years). The investigation conformed to the principles outlined in the Declaration of Helsinki and Title 45, U.S. Code of Federal Regulations, Part 46 and was approved by the New Zealand Multi-region Ethics Committee. Each participating patient provided written, informed consent.

The total number of subjects recruited was 2144. Of these, coronary artery angiography was performed at the time of presentation in 1643 subjects. The coronary arteries were seen to be normal in 105 subjects. In the remainder, abnormalities (thickening and irregularity, narrowing from plaque) were identified as typical of atheromatous vascular degeneration. Numbers of involved arteries were graded as one of four categories (0, no abnormality, 1, 2, 3 vessels abnormal), and the score used as an index of coronary artery involvement by arteriosclerosis.

After the index admission, and at the first follow up visit as an outpatient (5-56 days after angiography), a sample of venous blood was drawn into EDTA collection tubes (Becton-Dickinson, Plymouth, UK), and placed in an ice water slurry and centrifuged (2800 g for 10 min) within 10 min of collection. The aspirated plasma was then stored at minus 80° C. until measurement of CNP and NTproCNP. Height and body weight were measured.

Pregnancy Subjects

Values in healthy non pregnant women aged 20-40 yr and used for reference to values in pregnancy are shown in Table 1.

TABLE 1

Plasma NTproCNP (pmol/L) in age matched non-pregnant healthy volunteers

| Subject | Age (yr) | NTproCNP (pmol/l) | CNP (pmol/l) |
| --- | --- | --- | --- |
| n1 | 21.5 | 24.2 | 0.64 |
| n2 | 21.8 | 16.0 | 0.37 |
| n3 | 23.1 | 21.3 | 0.51 |
| n4 | 24.0 | 19.4 | |
| n5 | 24.4 | 13.8 | 0.6 |
| n6 | 25.3 | 14.3 | 0.75 |
| n7 | 26.5 | 14.5 | 0.85 |
| n8 | 27.0 | 11.6 | 0.94 |
| n9 | 29.1 | 12.2 | 0.74 |
| n10 | 29.4 | 14.6 | 0.5 |
| n11 | 31.5 | 10.6 | 0.34 |
| n12 | 31.7 | 14.2 | 0.43 |
| n13 | 32.0 | 17.4 | 1 |
| n14 | 32.7 | 17.7 | 0.44 |
| n15 | 33.0 | 15.2 | 1.17 |
| n16 | 33.2 | 10.7 | 0.46 |
| n17 | 35.8 | 16.2 | 0.56 |
| n18 | 36.3 | 14.0 | 0.79 |
| n19 | 36.6 | 19.5 | 0.65 |
| n20 | 37.1 | 12.7 | 0.54 |
| n21 | 37.3 | 25.4 | 0.64 |
| n22 | 38.0 | 16.4 | 0.8 |
| n23 | 38.1 | 13.2 | 0.64 |
| n24 | 39.8 | 17.1 | 0.57 |
| n25 | 40.7 | 9.6 | 0.59 |
| mean | 31.4 | 15.7 | 0.65 |
| SD | 5.9 | 4.0 | 0.20 |

Fifty two (52) pregnant women in whom serial measurements of CNP peptides in maternal plasma were made throughout gestation and related to obstetric outcome were examined.

The study was designed to determine whether CNP (both CNP and NTproCNP) peptide concentrations in maternal plasma would increase as an adaptive response to (i) vascular insufficiency in the setting of the increasing demands of pregnancy, and/or (ii) restricted growth of the fetus. Furthermore, the study was designed to determine if there was a correlation between increase in CNP peptides and adverse obstetric event during pregnancy.

The study was conducted in Christchurch during the years 2011-13. All women received obstetric care supervised by staff of the Department of Obstetrics, Christchurch Women's Hospital (CWH). All measurements of CNP peptides were undertaken by Endolab Staff, CCERG, University of Otago, Christchurch. All studies were approved by the New Zealand Upper South B Regional Ethics Committee. Recruitment was sought from healthy pregnant women at the time of initial presentation to the Lead Maternity Career, and were enrolled after informed consent was obtained.

Exclusions included the following: major structural or chromosomal fetal abnormality or any maternal condition likely to be associated with alteration of growth pattern such as hypertension, renal or autoimmune disease or pre-existing diabetes. Fifty two (52) subjects were enrolled and studied throughout gestation which culminated in the delivery of a healthy infant in 50 of 52 subjects.

At enrolment, a complete medical and obstetric history, together with details of medication and smoking history were obtained. Measurements of blood pressure, height, paternal height, maternal weight pre-pregnancy and maternal Body Mass Index (BMI), were recorded at enrolment, and risk status (low or high risk of an adverse event) assigned on the basis of obstetric history, current health and routine blood testing (including PAPPA, and HCG). This review, together with subsequent care followed the guide lines of the Institutions "best practice" of antenatal care at the CWH.

Venous blood sampling for plasma CNP forms, oestradiol (E2), oestriol (E3) and CRH (corticotrophin releasing hormone) at enrolment (12-25 weeks) and subsequently at intervals of 4 weeks commencing at 20 weeks gestation.

Ultrasound measurement of standard growth parameters included biparietal diameter, head and abdominal circumference, crown rump length and femur length at enrolment 12-13 weeks, then at 24, 28, 32 and 36 weeks gestation. At 24 weeks, uterine artery Doppler scans were performed in all subjects to help predict subsequent risk of fetal growth restriction. Those with abnormal scans were monitored more closely as described below.

In addition to the usual scanning and routine blood testing as part of these guide lines, this research study called for the following additional procedures if not already undertaken:—ultra sound scanning at weeks 20, 24, 28, 32 and 36 weeks gestation; umbilical artery Doppler scans at intervals of 4 weeks between 24-36 weeks gestation; uterine artery Doppler scans at 24 weeks; and blood sampling for maternal plasma CNP and amino terminal proCNP (NTproCNP) at enrolment (where possible at approximately 16 weeks) and in most subjects at intervals of 4 weeks thereafter.

A final sample of blood was drawn for maternal plasma CNP forms, umbilical plasma for CNP forms, IGF-1 insulin and adiponectin immediately post-partum. In selected cases, macroscopic and histological examination of the placenta was undertaken as clinically appropriate and sectors excised as described by (Wyatt S M et al (2005) 26(5):372-9) and deep frozen for subsequent measurements of CNP peptides.

High Risk Pregnancy Subjects

High risk pregnancies were recruited in two ways. First, some (the majority) were identified at the 1st visit using well defined criteria and routine exam findings. Second, recruitment occurred in subjects presenting with complications later in pregnancy. For the purposes of this study, fetal compromise was evidenced by one or more of the following:

1) ultra sound signs of abnormal fetal growth 2) abnormal fetal or uterine Doppler blood flow and 3) oligohydramnios in the absence of membrane rupture. Data collection at and following enrolment proceeded as detailed above. Subjects with impaired uterine blood flow (either elevated resistance index>$95^{th}$ centile or notched waveform) were subsequently more closely monitored and had additional ultra sound examinations at 34 weeks and as clinically appropriate. Post-partum procedures followed as described above.

Twenty eight subjects all of whom had one or more adverse event following enrolment—had proceeded through the study protocol. For the purposes of this study, an adverse event was defined as an abnormality detected by ultra sound scanning warranting further investigation, and or an obstetric related complication warranting urgent specialist review and hospitalisation. Endpoints used to define an adverse event are described in Table 2 below.

TABLE 2

Endpoints used to define an adverse obstetric event

| | |
|---|---|
| Small gestational age (SGA) | Live baby with birth weight <5th percentile using customised data, or a fetus equal or less than the 5th centile using customised charts corrected for gestational age. |
| Large gestational age (LGA) | Live baby with birth weight >95th percentile using customised data, or a fetus equal or greater than the 97th centile using customised charts corrected for gestational age. |
| Pre-term delivery | Live birth prior to 37 weeks. |
| Spontaneous pre-term delivery | Defined as a vaginal delivery of a live baby prior to 37 weeks where labour has not been induced. |
| Threatened pre-term delivery | Defined by need for hospitalisation for signs and symptoms consistent with the diagnosis and requiring corticosteroid administration prior to 37 weeks. |
| Fetal loss | Defined by miscarriage before 20 weeks, or intra uterine fetal or perinatal death after 20 weeks. |
| Reduced fetal growth | Defined by estimated fetal weight equal or less than the 5th centile using customised charts and corrected for gestational age, and/or a fall of 20 centile points in estimated fetal weight over 4 weeks or corresponding change over longer time periods. |
| Excessive fetal growth | Defined by estimated fetal weight greater than the 95th centile using customised charts and corrected for gestational age, and/or a rise of 20 centile points in 4 weeks in estimated fetal weight or corresponding change over longer time periods. |
| Hypertension | Defined by diastolic pressures equal or >90 or systolic equal or >140 at any time during gestation irrespective of pre-existing presence of raised blood pressure or treatment. |
| Pre-eclampsia | Defined by diastolic pressures equal or >90 or systolic equal or >140 at any time during gestation but with the addition of proteinuria (>3 mg/mmol of creatinine). |
| Prepartum HELLP syndrome | Defined in the obstetric literature. |
| Placental abruption | Defined by clinical criteria after 20 weeks gestation. |
| Hyperglycaemia (GDM) | Defined by fasting glucose equal or >5.5, or equal or >9 at 2 hr after a 75 g load. |
| Ante partum haemorrhage | Defined as any clinically significant bleeding in pregnancy after 20 weeks of gestation. |
| Oliohydramnios/ polyhydramnios | Defined by values using 5th and $95^{th}$ centiles. |
| Abnormal Doppler scans | Defined as those scans showing umbilical artery resistance index >95th, and or middle cerebral artery <5th centile at any time in gestation. |

Classification of an Adverse Obstetric Event

End points constituting an adverse event were drawn up by the study group prior to the availability of CNP measurements, and are listed in Table 2 above. End points were selected on the basis of (i) accepted threats to fetal maternal welfare commonly encountered in obstetric practice and (ii) the ability to detect the threat in the course of the monitoring procedures in place during gestation. In the event, 28 subjects met one of these pre-defined end points (Group C, complicated pregnancies). Details of these adverse events, the numbers of women affected by the event and the timing of the events first presentation are listed in Table 3. The remainder (Group N, normal pregnancy) comprise 24 subjects whose gestation was largely uneventful. Specifically, none of these subjects experienced any of the endpoints listed in Table 2.

TABLE 3

Summary of adverse obstetric events in 28 subjects*

| Event | Gestational age** |
|---|---|
| SGA (n = 8) | 24; 24; 25; 32; 32; 36; 41(T); 41(T) |
| High BP (n = 10) | 12; 12; 14; 24; 24; 30; 36; 36; 37; 38 |
| GDM (n = 4) | 28; 28; 28; 24 |
| LGA (n = 3) | 36; 39(T); 38 |
| Threatened pre term delivery (n = 3) | 33; 35; 35 |
| Pre-term delivery (n = 2) | 33; 36 |
| Polyhydramnios (n = 3) | 29; 37; 39 |
| Oligohydramnios (n = 3) | 32; 37; 38 |
| Placental abruption (n = 2) | 22; 23 |
| Placental trauma (n = 1) | 23 |
| Pre eclampsia (n = 1) | 38 |
| HELLP syndrome (n = 1) | 38 |
| Dysmorphic fetus (n = 1) | 20(T) |
| Intra uterine fetal death (n = 1) | 34 |

*some subjects had more than one adverse event.
Bracketed numerals are number of subjects.
**Age (weeks) when adverse event presented.
(T)indicates at delivery.

Plasma Assays

Plasma creatinine was determined by the Architect c8000 analyser (Abbott Laboratories, USA) and was used to calculate glomerular filtration rate (eGFR) Levey A S et al (1999) 1306):461-70). Plasma NTproCNP was measured by radioimmunoassay as previously described (Prickett T C R et al (2001) Biochemical & Biophysical Research Communications 286(3):513-517; Prickett T C R et al (2005) Pediatric Research 2005 58(2):334-340) with the following alterations: 100 µl of standard or sample extract was pre-incubated with 50 µl primary rabbit antiserum (J39) raised against synthetic human proCNP1-15 (diluted to 1:6,000) and incubated for 22 to 24 h at 4 C. The antiserum J39 epitope on proCNP spans amino acid residues 3-15. Fifty microliters of radiolabelled tracer (1,500 cpm) was then added and incubated for a further 24 h at 4 C. The detection limit of this assay is 1.2 pmol/L (0.3 pmol/L after sample concentration). Within- and between-assay coefficients of variation are 6.8% and 8.4%, respectively, at 14 pmol/L. Cross-reactivity with ANP propeptide in this assay is <0.07% and with human BNP propeptide is <0.4%. CNP was also measured by radioimmunoassay as previously described (Yandle T G et al (1993) Peptides 14(4):713-716) using a commercial CNP-22 antiserum provided by Phoenix Pharmaceuticals, Belmont Calif. Within- and between-assay coefficients of variation were 3.8% and 5.5% respectively at 9 pmol/L. The detection limit was 0.5 pmol/L. CNP and NTproCNP SDS were determined using the reference ranges the inventors have previously described (Olney R C et al (2012) Clin Endocrinol (Oxf) 21 Mar. 2012 doi: 10.1111/j.365-2265.2012.04392.x).

Placental tissues zones (maternal ie decidual surface, fetal ie chorionic surface and intervening zone) were extracted (Yandle et al, supra) prior to assay then measured as described above. Values are expressed as fmol/g tissue extracted.

Statistical Analyses

Results are expressed as median (interquartile range, IQR) or as means with SD or SEM as indicated in the text. Spearman rank coefficient was used to determine correlations between variables, presented as r values. Statistical significance was assumed when p<0.05. Multivariable linear regression analysis was performed using a backward stepwise approach considering factors that were significant at r>0.2 level by univariate analysis. Reference range curves for CNP and NTproCNP were estimated by the LMS procedure (Cole T J (1990) Eur J Clin Nutr 44(1):45-60), using LMS Chart Maker software (version 2.4, Harlow Printing Limited, South Shields, UK).

EXAMPLE 1 Analysis of NTproCNP and CNP Peptides in Normal Healthy Controls

Characteristics of the subject population are summarised in Table 4. The overwhelming majority were Caucasian (91.2% European, 2.7% Maori or Pacific Islander and 6.1% other, or unknown). Compared to US population norms (McDowell M A et al (2008) National Health Statistics Reports 10:1-45) adult height is similar but BMI is significantly lower (p<0.005). Of the total group, one or more of three (self-reported) vascular risk factors (smoking (n=25 subjects), hypertension (n=51), lipid disorder (n=32)) were present in 33%. In the remainder (67%) no vascular risk factor was present. Three subjects were diabetic (all type 2).

TABLE 4

Subject characteristics of normal subjects

| Characteristics | |
|---|---|
| Age, y, median (range) | 56 (21-80) |
| Gender, female n (%) | 139 (54%) |
| Weight, kg, median (IQR) | 75 (65-86) |
| Height, m, median (IQR) | 1.68 (1.62-1.75) |
| BMI, median (IQR) | 26 (23-29) |

(IQR), inter quartile range

CNP Forms and Effects of Age and Gender

Figure 2:
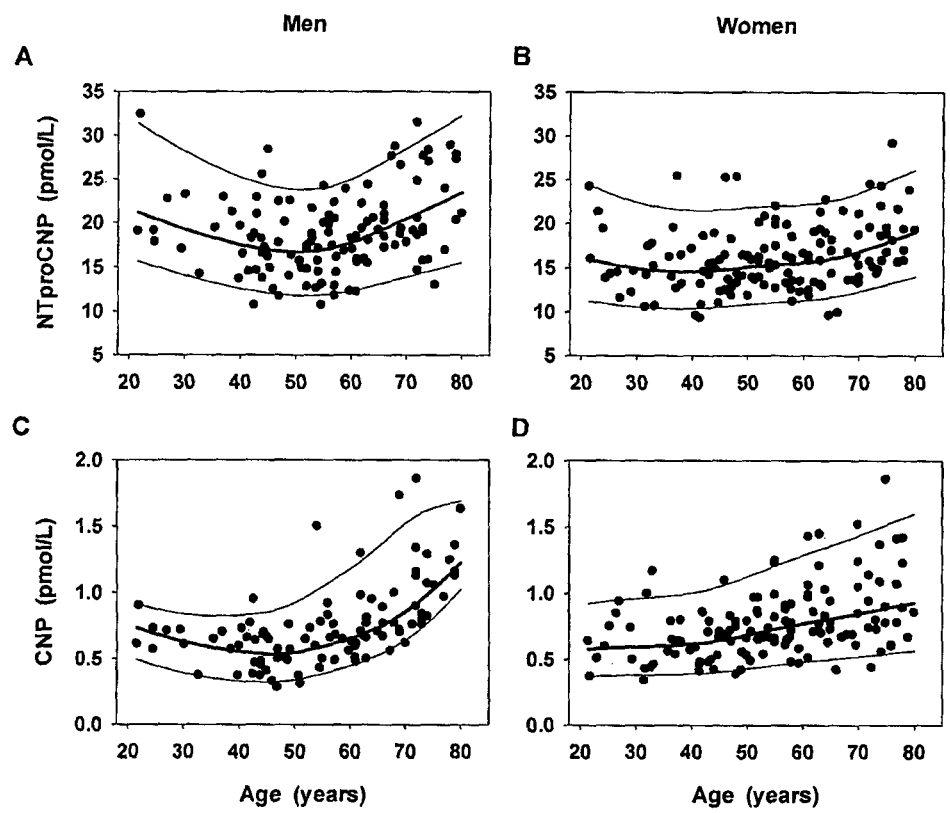
FIG. 2 shows variations in plasma NTproCNP (A and B) and CNP (C and D) with age in men (L) and women (R). Heavy line, median; lines $5^{th}$ and $95^{th}$ percentiles.

Plasma concentrations of NTproCNP and CNP in individual subjects were significantly correlated (r=0. 32, p<0.001). As shown in FIG. 2, median plasma NTproCNP and CNP declined in men to reach a nadir in the 5$^{th}$ decade after which levels increased progressively. In women both the initial decrease during decades 3-5 and the upward trend in median values after the 5$^{th}$ decade were less than in men. Over the age range 21-80y, both NTproCNP (r=0.24, p<0.001) and CNP (r=0.49, p<0.001) were correlated with age (Table 5).

TABLE 5

Correlations with natriuretic peptide forms.

| | NTproCNP | | CNP | | NTproBNP | | BNP | |
|---|---|---|---|---|---|---|---|---|
| Age | **0.24 ** | (258) | **0.49 ** | (229) | **0.38 ** | (137) | **0.21 *** | (137) |
| Weight | 0.05 | (242) | −0.05 | (218) | −0.06 | (137) | −0.04 | (137) |
| BMI | 0.06 | (242) | 0.07 | (218) | −0.03 | (137) | −0.01 | (137) |
| Creatinine | **0.56 ** | (204) | 0.11 | (181) | 0.03 | (134) | 0.06 | (134) |
| eGFR | **−0.29 ** | (204) | **−0.30 ** | (181) | **−0.32 ** | (134) | **−0.26 *** | (134) |
| bALP | **0.22 *** | (97) | 0.05 | (97) | — | | — | |
| Vascular risk score | **0.14 *** | (242) | **0.22 *** | (218) | 0.17 | (137) | 0.12 | (137) |

Data are Spearman's correlation coefficients.
Bracketed values are number of subjects
Significant correlations emboldened.
* p < 0.05,
** p < 0.001

Median concentration of NTproCNP was higher in men than in women (p<0.001) whereas CNP did not differ between the genders (p=0.3) (Table 6). In each decade, median plasma NTproCNP in men exceeded values in women whereas in years 30-70, CNP was higher in women.

TABLE 6

Effect of gender on circulating concentration of natriuretic peptides

| | Women | Men | P |
|---|---|---|---|
| CNP (pmol/L) | 0.72 (0.6-0.9) | 0.70 (0.57-0.84) | 0.28 |
| NTproCNP (pmol/L) | 15.8 (13.7-18.8) | 18.4 (15.9-21.0) | <0.001 |
| BNP (pmol/L) | 6.0 (3.6-8.0) | 4.3 (2.8-6.4) | <0.05 |
| NTproBNP (pmol/L) | 20.8 (11.1-33.9) | 12.3 (7.6-20.0) | <0.01 |

Values are medians with inter quartile range

Relation to Height and BMI

Figure 3:
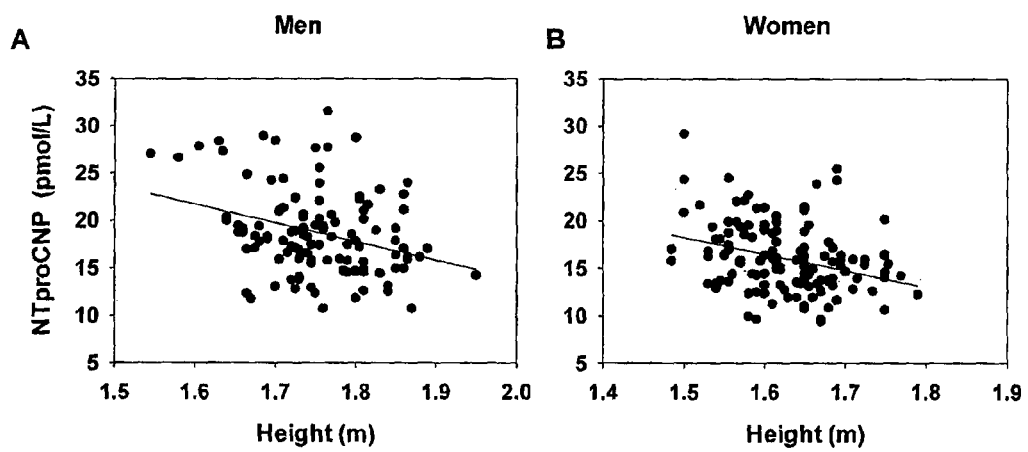
FIG. 3 shows Correlation of plasma NTproCNP concentrations with height in men, $r=-0.27$, $p<0.001$ (A) and women $r=-0.32$, $p<0.001$ (B).

For all subjects, there was no correlation of NTproCNP with height. However, when gender was analysed separately, adult height showed an inverse correlation with NTproCNP both in men (r=−0.27, p<0.001) and women (r=−0.32, p<0.001) (FIG. 3). Corresponding r values for CNP were −0.25 (p<0.05) and −0.18 (p<0.05) in men and women respectively. No correlation of either peptide was found with BMI.

Relation to Renal Function

Figure 4:
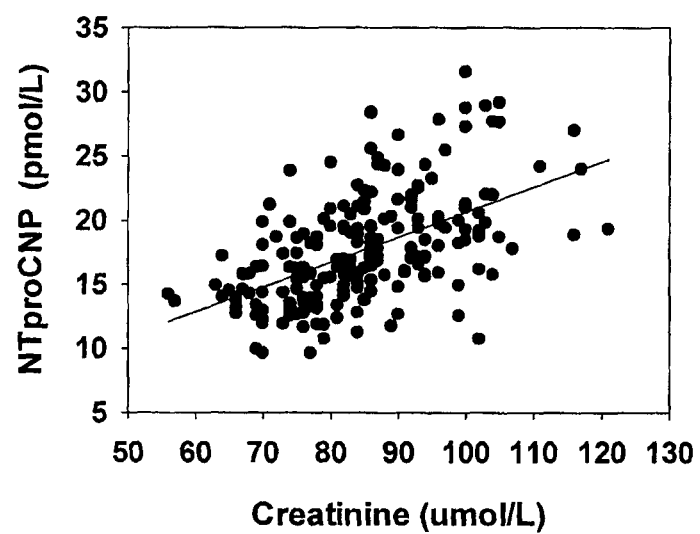
FIG. 4 shows correlation between plasma NTproCNP concentrations and creatinine in healthy volunteers aged 21-80 yrs, $r=0.56$, $p<0.001$. Line, regression line fit by the method of least squares.

As shown in FIG. 4, plasma NTproCNP was strongly correlated with plasma creatinine (r=0.56, p<0.001). The association of CNP with creatinine was not significant whereas both peptides were inversely and significantly associated with eGFR (p<0.001) Table 5).

After stepwise multiple linear regression, plasma creatinine, height and gender remained independently related to circulating concentrations of plasma NTproCNP, r=0.59. Collinearity amongst the variables in the following regression model were modest as indicated by variance inflation factors <2.3.

$$NTproCNP = 25.17 + (2.79 \times Gender) - (15.34 \times Height) + (0.17 \times creatinine)$$

Relation to Vascular Risk Factors

Plasma concentrations of CNP and NTproCNP were both positively related to the number of vascular risk factors present (r=0.22 and 0.14 respectively, p<0.05 for both, Table 5). In respect of hypertension alone (a highly significant risk factor) 51 reported a history of raised blood pressure. These subjects (all but 8 of whom were receiving treatment), had higher median levels of plasma NTproCNP [18 (16-22) versus 16 (14-19) pmol/L, p<0.01)] compared to those without history of raised blood pressure.

EXAMPLE 2 Analysis of CNP Peptides in Coronary Artery Disease Subjects

Figure 5:
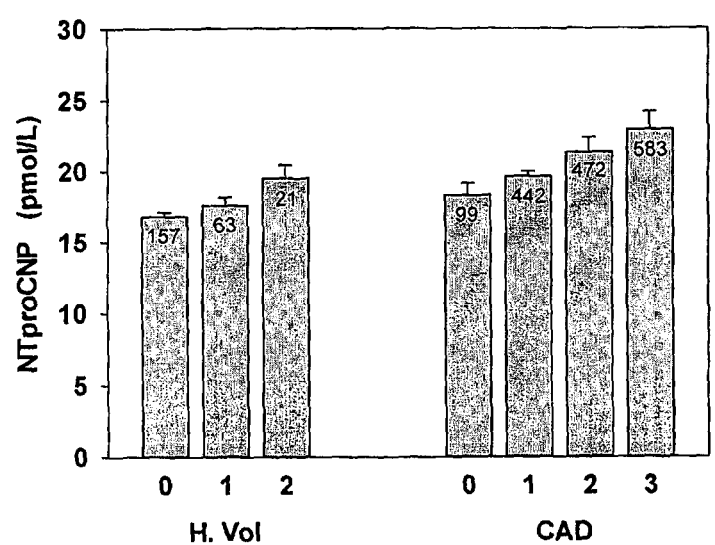
FIG. 5 shows human volunteers (H. vol) and coronary artery disease (CAD) cohorts are stratified by vascular risk factors and number of vessels involved respectively. Number of data points per bar is displayed within each bar. Data is displayed as mean±SEM.

Analysis of the relation between extent of coronary arterial involvement by atheroma and NTproCNP is shown in FIG. 5. Mean (SE in brackets) values of NTproCNP increased significantly with number of vessels involved (p<0.05); 18.3 pmol/L (0.84) with no vessels involved, 19.6 (0.37) with one, 21.3 (1.03) with two and 22. 8 (1.26) pmol/L with three vessels involved.

EXAMPLE 3 Maternal Plasma CNP Peptide in Pregnancy Subjects

Demographic and Clinical Data

There was no significant difference at enrolment between the normal (N) pregnancy and complicated (C) pregnancy groups with respect to maternal age (33.2 and 31.2 yr), height (165 and 165 cm), BMI (24 and 26), systolic (111 and 113) or diastolic (70 and 68 mm Hg) blood pressure respectively. Fifteen of twenty four (24) (64%) in Group N were nulliparous compared to 16 of 28 (57%) in Group C. Pregnancy was graded at enrolment as high risk in 15 of 24 (62%) Group N subjects and in 21 of 28 (75%) in Group C. Conception was induced in 3 of 28 Group C subjects and in one of 24 Group N subjects. Self-reported smoking was recorded in 3 and 4 subjects in Groups N and C respectively.

Plasma CNP Peptides

Figure 6:
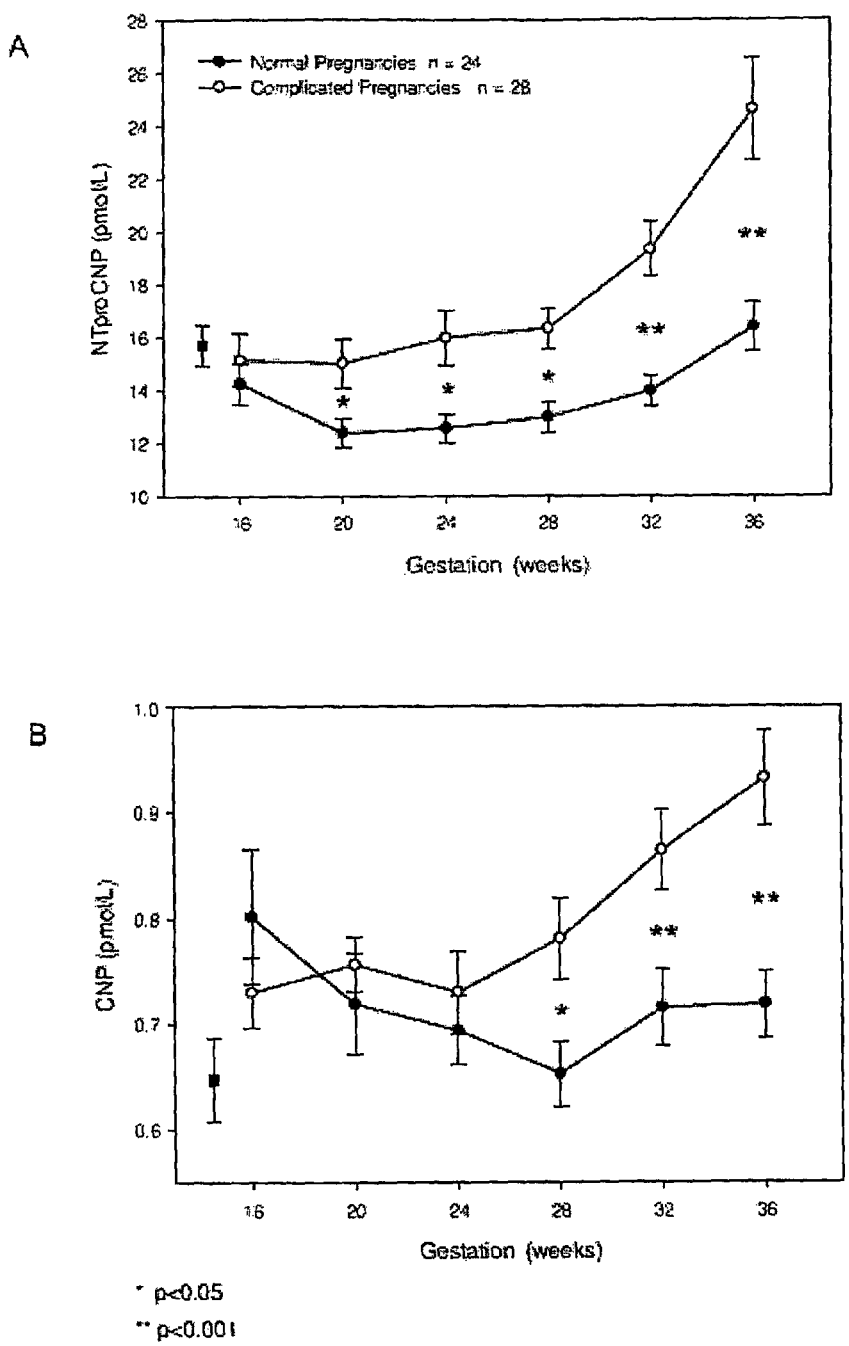
FIG. 6 shows serial maternal plasma NTproCNP (A) and CNP (B) concentrations in normal and complicated pregnancy. Values are mean (±SEM). Values in healthy age-matched non-pregnant women (filled squares) are also shown on the far left of each graph.
Figure 7:
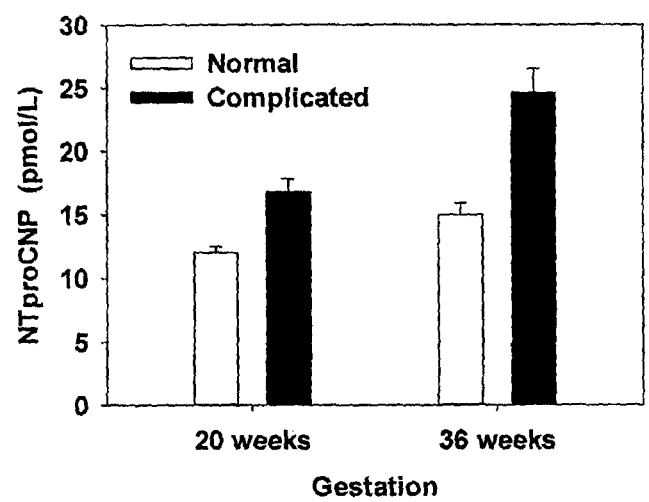
FIG. 7 shows maternal plasma concentrations of NTproCNP at 20 and 36 weeks respectively in normal (n=17) vs complicated pregnancies (n=21). Data is displayed as mean±SEM.

Serial changes in maternal plasma NTproCNP and CNP in Group N and Group C subjects are shown in FIG. 6. Data (mean and SEM) is plotted as visit number (1-6) corresponding to the most proximate gestational age in weeks (16, 20, 24, 28, 32 and 36 weeks respectively). Mean and SEM are also shown for healthy non pregnant women of the same age (FIG. 6). Respective values at weeks 20 and 36 for normal vs complicated pregnancies are shown in FIG. 7.

The following points are noted:
1. Compared to Group N, plasma NTproCNP values are significantly increased in Group C (analysis by ANOVA p<0.001).
2. Whereas values do not differ significantly at 16 weeks, plasma NTproCNP declines at 20 weeks in Group N but not in Group C.
3. Values of NTproCNP in Group N remain below initial values until 32 weeks.
4. In both groups, NTproCNP further increases after 28 weeks—more markedly in Group C.
5. With reference to Table 2 and FIG. 6, the significantly elevated concentration of NTproCNP in Group C subjects at 24 weeks occurs at a time when less than half of these subjects (12 of 28) have had the adverse event recognised.
6. Compared to plasma NTproCNP values (Table 1) in healthy non-pregnant women (15.7±0.8 pmol/l, n=25), values at 20 weeks gestation in Group N are significantly reduced (12.5±0.4 pmol/l, n=17, p=0.001).
7. Although plasma CNP is low (<1 pmol/l) and close to the levels of detection, concentrations in Group C significantly exceed those in Group N after 28 weeks gestation.

Association of CNP Values with Specific Adverse Events

A. High Blood Pressure

Ten subjects had an elevated systolic or diastolic pressure at some point in gestation. An additional subject had all the hall marks of preeclampsia but with no elevation in blood pressure. This subject with HELLP syndrome is therefore considered here since the vascular disorder in this syndrome is similar to that observed in pre-eclampsia. In 5 of the 10 with a raised blood pressure, no event other than an abnormal pressure was identified. Maternal plasma NTproCNP in these 5 subjects are shown in Table 7A, along with the gestation age (nearest week) when the abnormal pressure was first detected. As shown in the table, plasma. NTproCNP levels approximated values seen in Group N in 3 subjects, whereas in 2, values increased in late gestation. One can conclude that a finding of a pressure at or above 140 systolic or 90 diastolic does not in itself necessarily increase maternal NTproCNP. In contrast to these findings, 2 of the 10 subjects with a raised blood pressure—and the subject with HELLP syndrome—exhibited a severe adverse event. Their NTproCNP values are listed also in Table 7B.

TABLE 7

Plasma NTproCNP concentrations (pmol/L) in patients with raised blood pressure. Emboldened values depict the time at which elevation was first detected.

| | Gestation (weeks) | | | | | |
|---|---|---|---|---|---|---|
| Patients | 16 | 20 | 24 | 28 | 32 | 36 |
| A. No other abnormal events | | | | | | |
| p7 | 11.8 | 12.4 | 13.3 | 12.6 | 14.3 | 15.2 |
| p10 | ND | | 8.6 | 11.5 | 13.1 | 13.1 |
| p16 | 12.5 | 9.9 | 11.7 | 11.2 | 13.2 | 14.8 |
| p23 | 14.9 | 14.5 | 15.7 | 17.2 | 21.3 | 26.9 |
| p25 | 11.9 | 13.3 | 12 | 17.2 | 18.9 | 21 |
| B. Associated with other events | | | | | | |
| p13 | | 14.7 | 15.2 | 20.7 | 20 | 38.3 |
| p14 | 16.2 | | 22.6 | 23 | 27.5 | 23.4 |
| p51 | | 19.7 | 22.0 | 20.1 | 29.2 | |

In subject p51, having exhibited normal indices including repeated levels of normal blood pressure and normal fetal growth, a sudden increase in blood pressure (157/100) was recorded at 38.8 weeks, together with signs of preeclampsia (increased urine protein and abnormal liver function tests) which required emergency induction of labour. Maternal plasma NTproCNP was already clearly elevated at 20 weeks, and continued to rise progressively to reach a value of 29.2 pmol/l at 32 weeks—ie 6 weeks before preeclampsia became clinically overt. In subject p13, blood pressure was normal throughout gestation but reduced fetal growth was detected at 24 weeks. Monitoring showed no other adverse event until at 37 weeks when clinical features of the HELLP syndrome suddenly developed requiring emergency section. In this subject, plasma NTproCNP had risen to 20.7 pmol/l at 28 weeks, then 38 pmol/l at 36 weeks—several weeks before the emergency was recognised. In subject p14, blood pressure was mildly elevated (140/80 at 24 weeks) and during later gestation, with fetal growth remaining normal throughout. However at 39 weeks, an emergency section was required following an ante partum haemorrhage and the appearance of signs of fetal distress. Unexpectedly the infant at birth was growth restricted. In this subject, plasma NTproCNP was clearly raised at 24 weeks (22.6 pmol/l), peaking at 27.5 pmol/l at 32 weeks. Thus in all 3 cases, plasma NTproCNP was markedly raised above those levels found in Group N—at least several weeks before standard monitoring procedures had raised concern.

B. Intra Uterine Growth Restriction (Small for Gestational Age, SGA).

Eight neonates with IUGR (birth weight <5%) were identified. In 3 of these 8 subjects (p15, p24.p 56), the growth disorder was an isolated finding whereas in 5 the restricted growth was associated with one or more additional adverse events. Individual values and mean maternal NTproCNP values for each of these 2 subgroups are shown in Table 8.

TABLE 8

Plasma NTproCNP concentrations (pmol/l) in patients with Intrauterine growth restriction

| Patient | Gestation (weeks) | | | | | |
|---|---|---|---|---|---|---|
| | 16 | 20 | 24 | 28 | 32 | 36 |
| A. No other abnormal events | | | | | | |
| p15 | 11.6 | 13.1 | 11.8 | 13.5 | 21.9 | 22.7 |
| p24 | | 13.0 | 14.0 | 17.3 | 14.9 | 14.3 |
| p56 | 14.6 | 10.8 | 9.0 | 11.0 | 16.0 | 15.7 |
| Mean | 13.1 | 12.3 | 11.6 | 13.9 | 17.6 | 17.6 |
| Sem | 1.5 | 0.8 | 1.4 | 1.8 | 2.2 | 2.6 |
| n | 2 | 3 | 3 | 3 | 3 | 3 |
| B. Associated with other events | | | | | | |
| p4 | | 12.8 | 14.1 | 13.0 | 18.2 | 26.8 |
| p9 | | 17.1 | 16.7 | 13.5 | 14.5 | |
| p13 | | 14.7 | 15.2 | 20.7 | 20.0 | 38.3 |
| p14 | 16.2 | | 22.6 | 23 | 27.5 | 23.4 |
| p27 | | | 13.9 | 13.6 | 15.3 | 24.3 |
| Mean | 16.2 | 14.9 | 16.5 | 16.8 | 19.1 | 28.2 |
| Sem | — | 1.2 | 1.6 | 2.1 | 2.3 | 3.4 |
| n | 1 | 3 | 5 | 5 | 5 | 4 |

In the 3 subjects with isolated IUGR (Table 8A), NTproCNP values at 32 weeks had increased to levels above those observed in Group N. In one of these (p15), estimated fetal weight (EFW) was at the $95^{th}$ percentile at 24 weeks, $50^{th}$ percentile at 28 and 32 weeks, falling to $25^{th}$ percentile at 36 weeks. Plasma NTproCNP increased abruptly from 13.5 pmol/l at 28 weeks to 21.9 at 32 weeks and remained increased (22.7 pmol/l) at 36 weeks even though EFW remained well within normal limits. At birth (41 weeks) birth weight (BW) was $<5^{th}$ percentile. In a second case (p24), EFW at 24 weeks was at the $20^{th}$ percentile, $40^{th}$ percentile at 28 weeks, falling to $<5^{th}$ percentile at 32-36 weeks. Maternal plasma NTproCNP values were normal (13-14 pmol/l) at 20-24 weeks but increased to 17.3 at 28 weeks i.e. before detection of any fall-off in fetal growth. In the third case (p56), EFW was at the $10^{th}$, 20th, 35th and 20the percentile on weeks 24, 28, 32 and 36 respectively. Here plasma NTproCNP was close to levels observed in Group N until levels rose from 11 pmol/l at 28 weeks to 16 and 15.7 pmol/l at weeks 32 and 36 respectively. This increase is consistent with a response to developing IUGR which was only detected in this case after birth of the fetus.

Taken together, these results support the hypothesis that an increase in maternal plasma NTproCNP can be an adaptive response to a fall-off on fetal growth.

C. Accelerated Growth (Large for Gestational Age, LGA).

Infants born large at birth were identified in 3 of the 27 cases. In one (p1), the accelerated growth was associated with GDM which was identified at 28 weeks, and initially treated by diet alone. At 24 weeks, EFW was at the $90^{th}$ percentile, $80^{th}$ at 28 weeks, and $>95^{th}$ percentile at 34 weeks when insulin treatment was instituted. Maternal NTproCNP levels rose from 15.4 at 20 weeks to 18 pmol/l at 32-36 weeks. In the second case (p62), EFW was 85% at 24 weeks, increasing to >95% at 28 weeks where it remained. Plasma NTproCNP was 13.2-15 pmol/l in weeks 20-28, after which much higher values (21.6 and 23.2 pmol/l at weeks 32 and 36 respectively) were found. These associations are consistent with the view that the demands consequent to excessive fetal growth may stimulate CNP production. The third subject (p53) is especially instructive. This 32 year old nullip (i.e. never born a viable child), assessed as low risk, had an uneventful pregnancy until 33 weeks gestation when she was hospitalised acutely for threatened pre term delivery. She received standard care (bed rest, nifedipine iv, and betamethasone), and was later discharged to continue an active (but highly stressful) professional life which she pursued until an uneventful delivery some 6 weeks later. EFW at 24 weeks was at the $10^{th}$ percentile, increasing to $50^{th}$ at 28 weeks and $>95^{th}$ percentile at the time of threatened pre term delivery. Plasma NTproCNP at 20 weeks was raised (24.5 pmol/l), increasing markedly to 30.2 and 54.6 pmol/l at weeks 32 and 36 respectively. The combination of accelerated fetal growth (commencing around 24 weeks) and threatened pre term delivery—plus an excessively stressful working life—are presumably all factors in leading to the very large increase in maternal plasma NTproCNP. In the only other instance of "uncomplicated" pre term threatened delivery (p59)—which occurred at 35 weeks-plasma NTproCNP also increased from 10.7 to 16.9 pmol/l at 36 weeks.

D. Gestational Diabetes Mellitus (GDM).

Four women developed GDM. One showed accelerated fetal growth as detailed above. In the remaining 3 cases (p6, p9, p31), one (p6) developed GDM at 28 weeks when metformin treatment was started. EFW was 35% at 24 weeks, 40% at 28 and 60% at 32 weeks when insulin treatment was added. Here, plasma NTproCNP was raised (23.5-31.1 pmol/l) in weeks 16-24, levels falling to 15.8 and 13.4 pmol/l at weeks 28 and 32 respectively i.ee after treatment for diabetes was started. This temporal sequence suggests that the development of diabetes during pregnancy stimulates CNP which reduces as maternal glucose levels are restored towards normal. In another subject ((p9), diabetes was detected at 28 weeks—insulin treatment commencing at 32 weeks at which time a slowing in fetal growth was identified (EFW $<5^{th}$ percentile). Premature labour occurred spontaneously at 33 weeks delivering a growth restricted infant.

Maternal plasma NTproCNP was raised (17.1 pmol/l) at 20 weeks, declining thereafter to levels of 13-14 pmol/l in weeks 28-32 presumably as a response to the correction in maternal plasma glucose levels. The third subject (p31) was receiving metformin for polycystic ovary syndrome but ceased this treatment at the time of enrolment. At 26 weeks, GDM was diagnosed and metformin was restarted at 28 weeks. Around week 36 her blood pressure rose to 172/117 at which time she was hospitalised and treated with methyl dopa to lower blood pressure. There was no evidence of preeclampsia. Spontaneous pre term delivery occurred at 36.9 weeks. In this subject EFW increased from 30% at 25 weeks to 80% at 32 weeks, and subsequently fell to 30% at term. Plasma NTproCNP rose from 14.4 pmol/l at 24 weeks to 18.2 pmol/l at 28 weeks—then fell to 15.6 pmol/l at 32 weeks after treatment for diabetes was started. Of note, the level was much increased (24.5 pmol/l) at 36 weeks at the time her blood pressure had risen just before delivery. Together these findings strongly suggest that NTproCNP is increased in uncontrolled diabetes during gestation, and falls with treatment. These observations further confirm the association of increases in blood pressure with increase in plasma NTproCNP.

E. Placental Abruption.

One subject (p2) presented with abruption at 28 weeks. Pregnancy was relatively uneventful until 24 weeks when she was hospitalised for vaginal bleeding. Bed rest was advised but some 2 weeks after discharge (GA 28 weeks) she was readmitted with clinical features of placental abruption now verified by ultrasound. Betamethasone was administered. Labour was induced at 36 weeks. Placental histology showed features of an old marginal placental (retro-membranous) haematoma without evidence of vascular infarction or maternal vasculopathy. In this subject maternal plasma NTproCNP was normal (10-14.3 pmol/l in weeks 16-24). At 28 weeks, a low value (8.6 pmol/l) was found, corresponding to betamethasone given 24 hr previously. A subsequent value at 32 weeks was normal (12.8 pmol/l). Thus in this subject plasma NTproCNP was normal except for the expected brief period of suppression after high doses of glucocorticoids. The finding of normal levels is consistent with the benign placental histology, and absence of vascular insults such as infarction/ischaemia.

F. Association of Raised NTproCNP with Placental Pathology.

Figure 8:
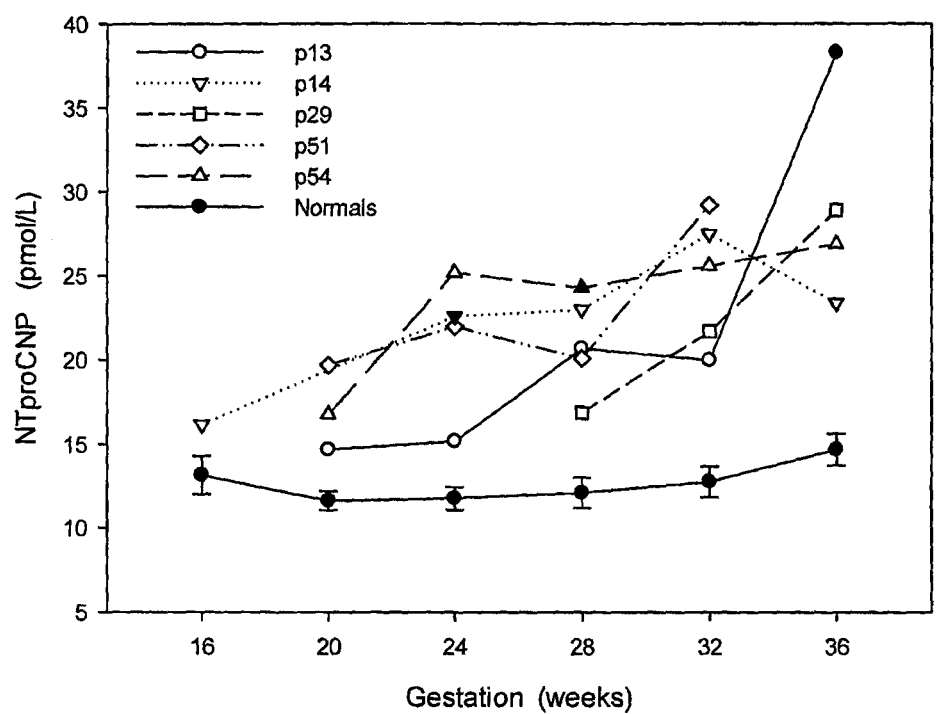
FIG. 8 shows rise in plasma NTproCNP concentration in patients with placental pathology. Filled symbols identify time of pathological event compared with serial changes in normal gestation (filled circles, mean±SEM n=11).
Figure 9:
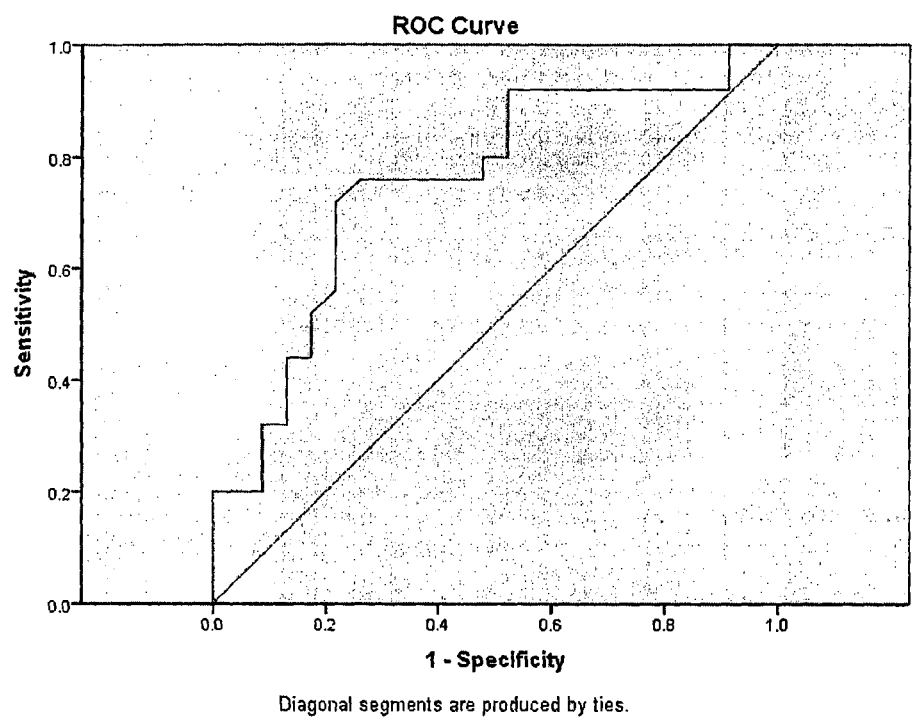
FIG. 9 shows sensitivity and specificity for NTproCNP measurements at 24 weeks gestation in predicting complications in pregnancy.

Although not nominated as an endpoint in this study, it is instructive to examine any association of maternal CNP levels with the anatomical findings as determined by an expert placental histologist. In 4 subjects (p13, p51, p54 p14) detailed reports of placental histological findings were available for analysis. In 3 of these 4, a severe (vascular) adverse event had occurred associated with marked increase in blood pressure or the HELLP syndrome. In all 3 cases (p13, p14, p51) there was evidence of fetal vasculopathy, patchy villitis or poorly vascularised villi. In the fourth, marked placental calcification involving villi was noted together with evidence of villous hypoplasia consistent with under-perfusion of the placental bed, and maternal hypoxia. The changes in maternal plasma NTproCNP in these 4 subjects, along with a fifth (p29) who suffered a traumatic placental haemorrhage/infarction at 23 weeks, are shown in FIG. 8. Mean values increased from 17.1 pmol/l at 20 weeks to 21.3 at 24 weeks, rising to 29.4 pmol/l at 36 weeks-much higher than levels found in normal pregnancy. Collectively these changes correlate with the placental vasculopathy objectively observed in 4 of the 5 cases. Notably plasma NTproCNP in these subjects was elevated as early as 24 weeks and predating the recognition of any vascular disorder.

Associations of CNP Values with Clinical Findings in the Normal Group

Categorising this group as normal follows from the fact that none of these pregnancies exhibited any of the pre-defined endpoints. It is therefore important to examine any association of maternal NTproCNP with possible events that were not endpoints of the study—for example interval aberrations in fetal growth velocity that did not manifest as a growth disorder at birth. The following subgroups were therefore reviewed.

A. Slowing of Fetal Growth During Gestation.

Using arbitrary definitions (any EFW <5%, or an interval fall off in growth as indicated by a fall of >20 EFW customised percentage points within a 4 week period), there are 6 cases to review (p22, p26, p58, p60, p63, p66). Mean values are listed in Table 9.

TABLE 9

Plasma NTproCNP (pmol/L) in subjects showing an interval slowing in fetal growth

| Patient | Gestation (weeks) | | | | | |
|---|---|---|---|---|---|---|
| | 16 | 20 | 24 | 28 | 32 | 36 |
| p22 | 11.1 | 11.9 | 11.1 | 14.5 | 13.9 | |
| p26 | | | 10.1 | 12.4 | 9.6 | 12.7 |
| p58 | 13.8 | 13.9 | 12.2 | 9.9 | 13.1 | 12.6 |
| p60 | | 10.6 | 14.5 | 15.6 | 16.2 | 18.5 |
| p63 | | 10.2 | 11.5 | 11.1 | 11.8 | 15.9 |
| p66 | | 12.2 | 12.1 | 11.8 | 16.2 | |
| Mean | 12.5 | 11.8 | 11.9 | 12.6 | 13.5 | 14.9 |
| Sem | 1.4 | 0.7 | 0.6 | 0.9 | 1.0 | 1.4 |
| n | 2 | 5 | 6 | 6 | 6 | 4 |

Values did not differ significantly from the remaining 18 in group N without an interval fall in fetal growth. These results suggest that relatively small interval falls, as detected by customised EFW indices, do not perturb maternal plasma NTproCNP values when pregnancy is otherwise normal.

B. Accelerated Gains in Fetal Growth.

Again using arbitrary definitions (any EFW >95%, or an interval increase in growth as indicated by a rise of >20 EFW customised percentage points within a 4 week period), there are 5 cases to review (p20, 21, 55, 61, 67). One of these (p21) is considered as an outlier (see below). Table 10 shows the individual and mean values in these 5 subjects. Excluding the outlier, values show a greater upward trend than seen in the normal Group without any interval growth disorder (see below and Table 11).

TABLE 10

Plasma NTproCNP (pmol/l) in subjects showing an interval of accelerated fetal growth

| Patient | Gestation (weeks) | | | | | |
|---|---|---|---|---|---|---|
| | 16 | 20 | 24 | 28 | 32 | 36 |
| p20 | | | | 12.8 | 13.7 | 14.7 |
| p21 | 18.6 | 17.7 | 19.8 | 18.0 | 18.8 | 27.9 |
| p55 | 14.6 | 15.4 | | 11.2 | 16.1 | 13.6 |
| p61 | 14.8 | 15.1 | 13 | 18.6 | 17.2 | 21.7 |
| p67 | | 10.7 | 11.4 | 12.6 | 14.2 | 17.2 |
| Mean | 16.0 | 14.7 | 14.7 | 14.6 | 16.0 | 19.0 |
| Sem | 1.3 | 1.5 | 2.6 | 1.5 | 0.9 | 2.6 |
| n | 3 | 4 | 3 | 5 | 5 | 5 |

C. Identifying Subjects in Group N without Interval Growth Disorder or Other Factors that Might Compromise Fetal Welfare but were not Endpoints.

In order to define an exclusively normal gestation, analysis was made of maternal NTproCNP values having excluded (i) those with an interval growth disorder and (ii) those with other unexpected events occurring before or during gestation which might have compromised fetal maternal health. On these grounds one subject with a single umbilical artery (p17) and one admitted with acute suppurative appendicitis (p60) were excluded. One further subject (p21, NTproCNP 18.6 pmol/l at 16 weeks) was excluded as her results lie outside the range of all others in Group N. This subject had the highest BMI (33, group N mean 24.3), and was graded high risk at enrolment. IUGR complicated her two previous pregnancies, one of which resulted in fetal death in utero at 38 weeks. For these reasons the subject requested an early induction at 37 weeks gestation. Thus outlying NTproCNP values, abnormal body weight and her past obstetric history fully justify the exclusion. Mean values for the remaining 11 subjects (p3, p5, p11, p12, p19, p20, p50, p52, p64, p68, p70) are listed in Table 11. Of note, mean values were lower than the means of 24 subjects categorised as Group N.

TABLE 11

Plasma NTproCNP (pmol/l) in Group N women who do not show an interval growth disorder or other factors that might compromise fetal welfare

| Patient | Gestation (weeks) | | | | | |
|---|---|---|---|---|---|---|
| | 16 | 20 | 24 | 28 | 32 | 36 |
| p3 | 10.9 | 9.8 | 9.9 | 9 | 8.9 | 10.5 |
| p5 | | 12.1 | 11.4 | 11.4 | 11.4 | 16.0 |
| p11 | 14.6 | 14.1 | 16 | 18.3 | 16.4 | 21.2 |
| p12 | | 10.1 | 10.7 | | | |
| p19 | | 11.5 | 11.5 | 11.5 | 11.9 | 14.4 |
| p20 | | | | 12.8 | 13.7 | 14.7 |
| p50 | | 9.8 | 8.5 | 9.3 | 10.7 | 12.0 |
| p52 | | 12.9 | 12.9 | 13.3 | 14.5 | 16.4 |
| p64 | 14.0 | 12.7 | 14.1 | | 16.5 | 15.7 |
| p68 | | | 10.4 | 10.9 | 8.5 | 11.7 |
| p70 | | | 12.3 | 12.5 | 15.3 | 14.5 |
| Mean | 13.1 | 11.6 | 11.8 | 12.1 | 12.8 | 14.7 |
| Sem | 1.1 | 0.6 | 0.7 | 0.9 | 0.9 | 1.0 |
| n | 3 | 8 | 10 | 9 | 10 | 10 |

Application of CNP Peptides in Predicting Complications in Pregnancy

The above results clearly show that the maternal concentration of NTproCNP in plasma is abnormally increased in subjects who later proceed to experience an adverse event. Unlike many tests currently employed for determining risk, NTproCNP appears to increase in response to a variety of adverse events, and not just those affecting fetal growth or abnormal blood pressure. Furthermore, increases occur early in gestation—frequently before any adverse event presents. Even though the total number of subjects studied here is small, it is already obvious that the plasma concentration of NTproCNP as early as 24 weeks has predictive value. Specificity and sensitivity of the test at 24 weeks is shown by the ROC curve in FIG. 10. The area under the curve (AUC) is 0.754 indicating that over 75% of subjects sampled at that time point can be accurately assessed. For values using a 13.3 pM cut-off, the positive predictive value is 78%. Using the "purified" normal group (11 subjects as listed in Table 11 and more likely representative of healthy pregnant women in the community), even better risk classification is obtained.

CONCLUSIONS

This study found that compared to uneventful normal gestation, the concentration of maternal plasma NTproCNP, from as early as 20 weeks, is significantly increased in pregnancies where an adverse obstetric event threatens fetal-maternal health (FIG. 6). Significantly, the increase in maternal NTproCNP in most subjects precedes the first sign of the adverse event, and may be evident as early as 20-24 weeks.

In uneventful normal gestation, maternal plasma NTproCNP concentration was significantly lower at 20-24 weeks gestation (p=0.001) than NTproCNP concentration found in non-pregnant healthy subjects of the same age, however NTproCNP levels in subjects prone to an adverse event were similar to higher than the NTproCNP levels in non-pregnant subjects.

The data showed that maternal plasma NTproCNP increases progressively after 28 weeks gestation in both normal and complicated pregnancy at the time of most rapid increase in fetal growth and consequential demands on the maternal circulation (FIG. 6).

Using the maternal concentration of plasma NTproCNP at 24 weeks to predict occurrence of an adverse event, it was found that a concentration of NTproCNP exceeding 13.3 pmol/L had a positive predictive value of 78% and that maternal plasma NTproCNP concentrations at 24 weeks less than 13 pmol/l had a negative predictive value of 74%.

The highest concentrations of maternal NTproCNP occurred in those subjects who later exhibited a severe adverse event based on a vascular disorder (pre eclampsia, HELLP syndrome, high blood pressure associated with a separate adverse event). Interestingly, increase in maternal plasma NTproCNP is even more marked if a subject with a single adverse event then develops a second (but different) adverse event.

When evaluated against serial changes in normal pregnancy (where interval growth disorder and or other unexpected event are excluded), changes of more than 4 pmol/l across an interval of 4 weeks at any period of gestation is strongly correlated with the subsequent development of an adverse event.

Since maternal plasma NTproCNP in subjects with raised blood pressure alone may often be normal, yet values are raised in those proceeding to complications, maternal levels of NTproCNP at any point in gestation may be used to distinguish hypertensive subjects at greater risk.

With regard to fetal growth, an increase in maternal NTproCNP precedes or is co incident with significant changes in fetal growth, either reduced or accelerated. Accordingly, raised maternal NTproCNP in the setting of poor fetal growth may be used to select pregnancies likely to benefit from treatments aimed to improve blood flow to the fetus.

With regard to gestational diabetes mellitus (GDM), plasma NTproCNP was increased in subjects prior to treatment, and was found to decrease following corrective treatment. These decreases in maternal plasma NTproCNP appear to be unique to the latter intervention, and run counter to the strong upward incline noted generally in complicated pregnancy.

Additionally, it was also found that plasma NTproCNP concentrations were increased prior to the development of threatened pre term birth.

Marked increased in maternal NTproCNP occurs in the setting of histologically evident placental hypoperfusion states such as ischaemia, infarction, villitis and fetal vasculopathy.

In contrast, maternal plasma CNP concentrations were more variable and it was found that prior to 28 weeks gestation, CNP levels (unlike NTproCNP) did not correlate with subjects preceding an adverse event. This may be explained by degradation of CNP in tissues during pregnancy.

Taking the above in account, in normal pregnancy, plasma NTproCNP levels normally decrease in early gestation and typically remain at levels below non-pregnant women at the same age. These changes are likely to be a response of the normal vasculature to reduced maternal peripheral arterial resistance which is known to occur in early gestation. The failure to show this distinctive fall may be a signature of those at risk of an adverse event. Increases in both CNP and NTproCNP peptides when complications occur during pregnancy are likely to be i) an adaptive response to failure of the circulation to meet the demands imposed by pregnancy and/or ii) a response to aberrant fetal growth.

Remarks

The current disclosure provides strong evidence that plasma NTproCNP is positively associated with vascular risk, adverse events during pregnancy and with overt (established) arteriosclerosis. Further, in healthy volunteer subjects, plasma levels of NTproCNP are higher in men than women, and increase in older age-especially in men, findings that are consonant with the recognised prevalence of arteriosclerosis in these settings. An unexpected finding in the healthy volunteer group was, the highly significant inverse association of plasma NTproCNP with adult height in both males and females—shorter subjects have higher levels. Of note, meta-analyses indicate that the incidence of coronary artery disease is increased in subjects with short stature. The observations by the inventors-reduced height, increased plasma NTproCNP and vascular risk provide evidence supporting NTproCNPs role as a biomarker of future vascular complications.

In the healthy volunteer group, and in previous studies (Schouten B J et al (2011) 32(4):797-804), the inventors found strong associations of plasma NTproCNP with plasma creatinine. Renal clearance of the peptide from plasma clearly affects the concentration in the systemic circulation, and needs to be considered when interpreting values in clinical settings. The renal vasculature is itself prone to arteriosclerosis which is likely to impair renal function. The summative effects (increased production of CNP within the renal arteriosclerotic vessels and decreased renal clearance of NTproCNP from plasma) will augment the increase in plasma NTproCNP, and may contribute to the increases observed in the later decades (see FIG. 2).

The present finding of higher plasma NTproCNP concentrations in subjects with increasing coronary artery involvement has not been previously reported. The results strongly suggest that there is a uni-directional increase, extending from somewhat lower values in those without overt disease (but with increased vascular risk) to higher values as atheroma load increases (FIG. 5). Higher concentrations as vessel involvement increases could result from increased CNP gene expression within the vessel wall (Casco V H et al (2002) Journal of Histochemistry & Cytochemistry 50(6): 799-809) or from increased efflux of peptide into the circulation as the endothelial barrier is damaged by the disease (Jones G T et al (2005) 42(3):237-46). For example, in the context of arteriosclerosis affecting the cerebral microvasculature, this damage impairs the blood brain barrier and facilitates release or entry of proteins. Importantly, recent work by the inventors shows that an abrupt increase in both CNP and NTproCNP concentrations in the systemic circulation occurs immediately after successful primary percutaneous coronary intervention in subjects requiring stent insertion for coronary artery disease. This is the first clear demonstration that efflux of these CNP peptides from coronary arteriosclerotic blood vessels can in fact acutely raise levels significantly in the systemic circulation. It will be important in future studies to observe changes in plasma NTproCNP during interventions that reduce atheroma, including those associated with statin therapy. Recent reports show that acute myocardial infarction itself aggravates arteriosclerosis (Dutta P et al (2012) Nature 487 (7407). Thus monitoring NTproCNP after a heart attack could be useful in following extension of the vascular disease, and may allow earlier interventions aimed to prevent progression of the vascular damage.

The most surprising set of observations in the current study are those relating to plasma NTproCNP in pregnancy. To the inventors knowledge, plasma NTproCNP (or other CNP propeptide) levels in early pregnancy have not been previously reported. Previous studies (Stepan H et al (1998) Journal of Perinatal Medicine 26(1):56-8 and Walther T et al (2004) Journal of Endocrinology 180(1):17-22) report that plasma CNP in mid and late gestation did not differ from values in non-pregnant women—nor was any difference in CNP found in pregnancy complicated by preeclampsia or intra uterine growth restriction (IUGR) when compared with normal pregnancy. The present findings with respect to maternal plasma CNP concentrations are similar. However, by measuring plasma NTproCNP a quite different picture emerges. In contrast to much lower levels at mid gestation in women who later proceed to an uneventful delivery, much higher values were found in those who later develop adverse events. Further, concentrations continue to rise impressively in the latter group as gestation proceeds-whereas increases were less evident in normal pregnancy. These differences cannot be attributed to reduced renal clearance as plasma creatinine did not differ in the two groups. Thus measurements of NTproCNP early in pregnancy would appear to have great potential in identifying women at risk, enabling improved focus and more efficient monitoring as well as the possibility of earlier treatment interventions.

Other significant findings relate to fluctuations in plasma NTproCNP values the inventors observed over time in complicated cases. For example, raised levels in subjects with gestational diabetes fell after successful treatment was instituted. In subjects developing preeclampsia features, values increased as blood pressure rose, and in both of these cases, placental CNP content (maternal zone) was 3-5 fold greater than in other cases. These results point to important applications of serial monitoring of plasma NTproCNP during gestation at least in subjects at risk. Of note, subjects who were rated as low risk (using state of the art assessments including pregnancy associated placental protein, PAPP-A) yet had high values of plasma NTproCNP at enrolment and subsequently incurred adverse events.

Unexpectedly, the range of adverse events identified in subjects exhibiting high NTproCNP levels was quite diverse, and included such seemingly unrelated pathologies as fetal growth aberrations, gestational diabetes, threatened pre term delivery, pre eclampsia and placental hypermaturity (see Table 4). This finding differs from the experience with several other blood biomarkers currently in use for assessing high risk pregnancies such as sflt-1 (a marker of pre eclampsia (Myatt L et al (2009) Journal of Thrombosis and haemostasis 7(3):375-84) and other natriuretic peptides, ANP and BNP (Sugulle M et al (2012) Hypertension 59(2):395-401) which are likely to reflect only cardiac load.

It seems likely that plasma NTproCNP is raised above normal even before conception in some women at high risk of pregnancy complications. Pregnancy is increasingly viewed as representing a major challenge to maternal vascular homeostasis (Myatt L et al, supra). Thus adverse events in gestation may be the first evidence of susceptibility to vascular insults later in life. For example, pregnant women exhibiting IUGR or pre eclampsia are at increased risk of developing ischaemic heart disease (IHD) or stroke when compared with those without these complications (Myatt L et al, supra). Collectively the present findings showing that NTproCNP is a marker for vascular vulnerability have implications across a broad range of human pathophysiology and fit with the concept that pre-existing subclinical vascular disease may manifest in early pregnancy.

Finally, as applies to many blood biomarkers, plasma NTproCNP values in adults are likely to be affected by factors outside the vasculature. For example, renal impairment will raise levels by reducing clearance from plasma. Raised concentrations are also likely in well-established heart failure (Wright S P et al (2004) Hypertension 43(1): 94-100) and in subjects with increased bone turnover (Schouten B J et al (2012) Clinical endocrinology 76(6): 790-6) and advanced cirrhosis (Koch A (2012) Clinical Biochemistry 45(6):429-35). However, the lack of diurnal changes across waking hours or day to day variation, lack of effect of food ingestion and relative stability with respect to collection and storage are all positive attributes which should facilitate clinical applications in practice—especially now that an age and gender related SDS range has been established.

The invention claimed is:

1. A method for diagnosing a pregnancy-related vascular disorder in a female subject, or for predicting a risk for acquiring a pregnancy-related vascular disorder in a female subject, comprising:
   (a) detecting binding in vitro between (i) a human amino terminal pro C-type natriuretic peptide (NTproCNP) that is present in a first biological sample obtained at a first time point from the female subject, and (ii) a binding agent that is capable of specifically binding to the human NTproCNP, and therefrom measuring a first level of NTproCNP;
   (b) detecting binding in vitro between (i) a human amino terminal pro C-type natriuretic peptide (NTproCNP) that is present in a second biological sample obtained from the female subject at a second time point that is later than the first time point and is during pregnancy, and (ii) the binding agent that is capable of specifically binding to the human NTproCNP, and therefrom measuring a second level of NTproCNP; and
   (c) comparing the first level of NTproCNP measured in (a) to the second level of NTproCNP measured in (b), wherein a statistically significant increase in the second level of NT pro CNP measured in (b) relative to the first level of NTproCNP measured in (a) indicates the subject has a pregnancy-related vascular disorder, or is at increased risk for acquiring the pregnancy-related vascular disorder, and thereby diagnosing, or predicting the risk of acquiring, the pregnancy-related vascular disorder in the subject,
      wherein the biological sample is blood, plasma, serum, or a combination thereof, and wherein the binding agent is an anti-NTproCNP antibody or an antigen binding fragment thereof.

2. The method of claim 1 wherein either or both of:
   (1) the second time point is at or after at least 24 weeks of gestation, and
   (2) the method is predictive of the pregnancy-related vascular disorder when (i) the second level of NTproCNP measured in (c) is a measure of circulating NTproCNP and is increased by at least about 25-33 delta percent relative to the first level of NTproCNP measured in (a) as a measure of circulating NTproCNP, and (ii) at least four weeks separate the first and second time points.

3. The method of claim 1 wherein said first time point is prior to pregnancy.

4. The method of claim 1 wherein said first time point is during pregnancy, wherein a statistically significant decrease in the second level of NTproCNP measured in (b) relative to the first level of NTproCNP measured in (a) indicates the subject has an uncomplicated pregnancy or an improvement in the pregnancy-related vascular disorder, or is at increased risk for acquiring the pregnancy-related vascular disorder, and thereby diagnosing, or predicting the risk of acquiring, the pregnancy-related vascular disorder in the subject.

5. The method of claim 1 wherein at least one of:
   (a) the binding agent that is capable of specifically binding to the human NTproCNP is an antibody or antigen-binding fragment thereof that is in solution, or
   (b) the binding agent that is capable of specifically binding to the human NTproCNP is an antibody or antigen-binding fragment thereof that is immobilized to a solid phase.

* * * * *